(12) United States Patent
Nishino et al.

(10) Patent No.: US 9,526,470 B2
(45) Date of Patent: Dec. 27, 2016

(54) RADIATION IMAGE CAPTURING SYSTEM AND DETECTOR WITH RESET LIGHT CONTROL

(71) Applicant: FUJIFILM Corporation, Tokyo (JP)

(72) Inventors: Naoyuki Nishino, Kanagawa-ken (JP); Yasunori Ohta, Kanagawa-ken (JP); Kouichi Kitano, Kanagawa-ken (JP); Naoto Iwakiri, Kanagawa-ken (JP); Haruyasu Nakatsugawa, Kanagawa-ken (JP)

(73) Assignee: FUJIFILM Corporation, Tokyo (JP)

(*) Notice: Subject to any disclaimer, the term of this patent is extended or adjusted under 35 U.S.C. 154(b) by 358 days.

(21) Appl. No.: 14/260,782

(22) Filed: Apr. 24, 2014

(65) Prior Publication Data

US 2014/0233700 A1 Aug. 21, 2014

Related U.S. Application Data

(63) Continuation of application No. PCT/JP2012/076081, filed on Oct. 9, 2012.

(30) Foreign Application Priority Data

Oct. 25, 2011 (JP) ................. 2011-234412

(51) Int. Cl.
*H01L 27/146* (2006.01)
*H01L 27/148* (2006.01)
(Continued)

(52) U.S. Cl.
CPC ............ *A61B 6/547* (2013.01); *A61B 6/12* (2013.01); *G01T 1/2006* (2013.01); *G01T 1/208* (2013.01);
(Continued)

(58) Field of Classification Search
CPC ............ A61B 6/00; A61B 6/12; A61B 6/42; A61B 6/52; A61B 6/54; A61B 6/547; A61B 6/56; H03K 21/00; H03K 21/08; H03K 21/38; G01T 1/00; G01T 1/16; G01T 1/17; G01T 1/20; G01T 1/2006; G01T 1/2018; G01T 1/24; G01T 1/246; G01T 1/247; G01T 7/00; H04N 1/00912; H04N 1/00915; H04N 1/00917; H04N 5/00; H04N 5/30; H04N 5/32; H04N 5/321; H04N 5/335; H04N 5/3355; H04N 5/341; H04N 5/351; H04N 5/369; H04N 5/374; H04N 5/3741; H04N 5/378; H01L 25/00; H01L 25/03; H01L 25/04; H01L 25/041; H01L 25/065; H01L 25/0655; H01L 27/00; H01L 27/02; H01L 27/0203; H01L 27/10; H01L 27/14; H01L 27/144; H01L 27/1446; H01L 27/146; H01L 27/1461; H01L 27/14609; H01L 27/14643; H01L 27/14658; H01L 27/14661; H01L 27/14663; H01L 27/14676; H01L 27/148; H01L 27/14806; H01L 27/14831; H01L 27/14893; H01L 31/00; H01L 31/02; H01L 31/02016; H01L 31/08; H01L 31/085; H01L 31/10; H01L 31/115

See application file for complete search history.

(56) References Cited

U.S. PATENT DOCUMENTS 5,905,772 A 5/1999 Rutten et al.
2007/0131843 A1 6/2007 Yokoyama et al.
(Continued)

FOREIGN PATENT DOCUMENTS

JP 2006-140592 A 6/2006
JP 4150079 B2 9/2008

OTHER PUBLICATIONS

International Search Report, issued in PCT/JP2012/076081, dated Jan. 8, 2013.
(Continued)

*Primary Examiner* — Anastasia Midkiff
(74) *Attorney, Agent, or Firm* — Birch, Stewart, Kolasch & Birch, LLP

(57) ABSTRACT

A radiation detection device has: a scintillator for converting radiation into fluorescence; a photoelectric conversion unit for converting the fluorescence into an electric signal; and a reset light source unit for exposing reset light to the photoelectric conversion unit. A system control unit has an optical reset disabling unit for, based on a reset disabling instruction, disabling the exposure of the reset light output from the reset light source unit.

17 Claims, 18 Drawing Sheets

(51) Int. Cl.
| | |
|---|---|
| H04N 5/30 | (2006.01) |
| G01T 1/20 | (2006.01) |
| G01T 1/24 | (2006.01) |
| G01T 7/00 | (2006.01) |
| A61B 6/12 | (2006.01) |
| A61B 6/00 | (2006.01) |
| H04N 5/351 | (2011.01) |
| H04N 1/00 | (2006.01) |
| G01T 1/208 | (2006.01) |
| G01T 1/17 | (2006.01) |
| H04N 5/335 | (2011.01) |
| H04N 5/32 | (2006.01) |
| H04N 5/374 | (2011.01) |
| H01L 25/065 | (2006.01) |
| H01L 31/02 | (2006.01) |
| G01T 1/40 | (2006.01) |

(52) U.S. Cl.
CPC ............. G01T 1/2018 (2013.01); G01T 1/246 (2013.01); G01T 1/247 (2013.01); H01L 27/14601 (2013.01); H01L 27/14676 (2013.01); H01L 27/14806 (2013.01); H04N 1/00917 (2013.01); H04N 5/351 (2013.01); A61B 6/42 (2013.01); A61B 6/4283 (2013.01); A61B 6/4494 (2013.01); A61B 6/467 (2013.01); A61B 6/486 (2013.01); A61B 6/487 (2013.01); A61B 6/504 (2013.01); A61B 6/54 (2013.01); G01T 1/17 (2013.01); G01T 1/20 (2013.01); G01T 1/24 (2013.01); G01T 1/40 (2013.01); G01T 7/00 (2013.01); H01L 25/065 (2013.01); H01L 27/146 (2013.01); H01L 27/14643 (2013.01); H01L 27/14658 (2013.01); H01L 31/02016 (2013.01); H04N 5/32 (2013.01); H04N 5/335 (2013.01); H04N 5/3741 (2013.01)

(56) References Cited

U.S. PATENT DOCUMENTS

| | | | | |
|---|---|---|---|---|
| 2012/0119097 | A1* | 5/2012 | Nishino | G01T 1/2018 250/370.08 |
| 2012/0126124 | A1* | 5/2012 | Nakatsugawa | A61B 6/548 250/363.01 |
| 2012/0126129 | A1* | 5/2012 | Nakatsugawa | A61B 6/548 250/369 |
| 2012/0267535 | A1* | 10/2012 | Nakatsugawa | G01T 1/2002 250/362 |

OTHER PUBLICATIONS

Written Opinion of the International Searching Authority, issued in PCT/JP2012/076081, dated Jan. 8, 2013.

Foreign Office Action of Japan Patent Application No. 2013-540713 dated Mar. 17, 2015.

* cited by examiner

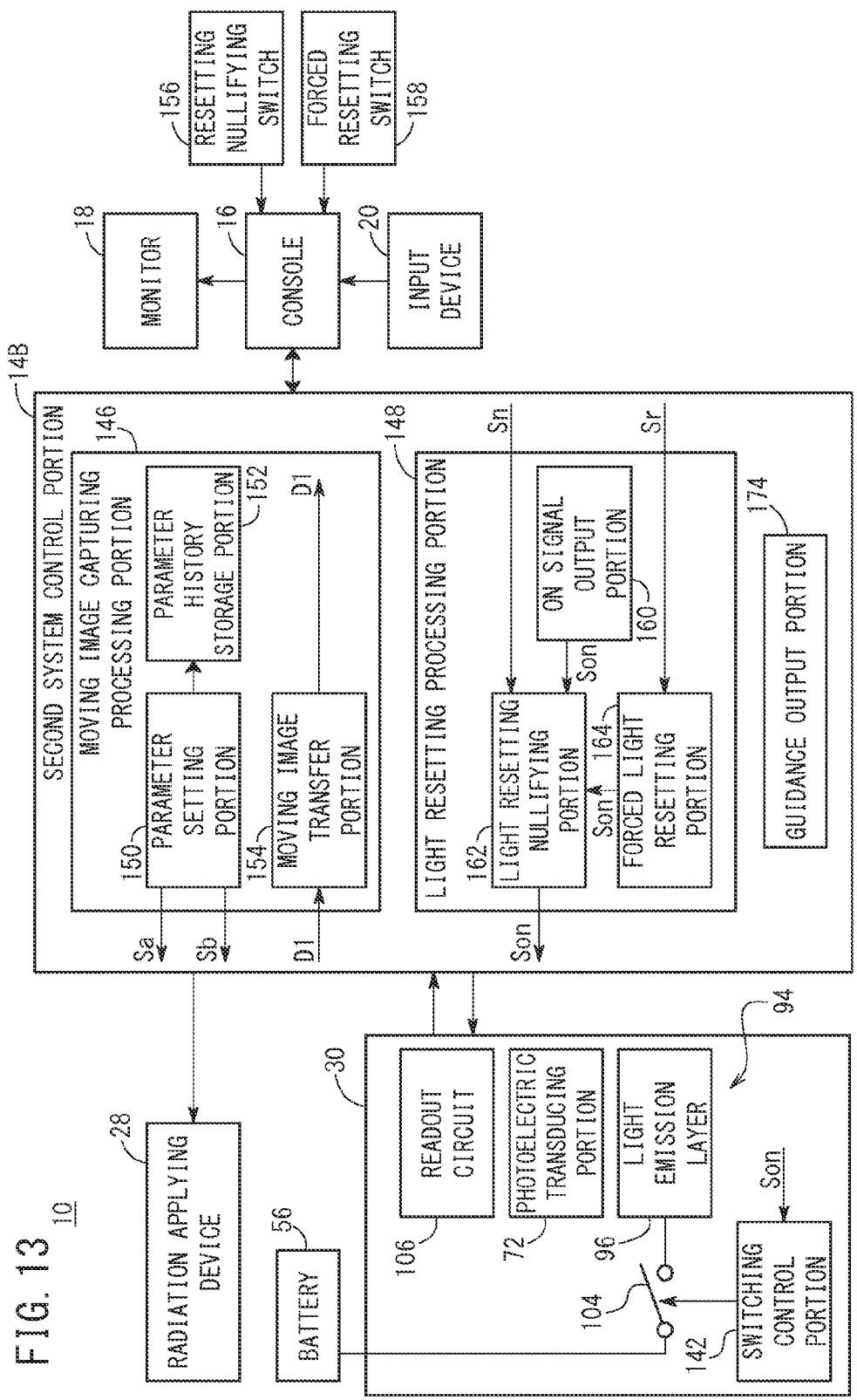

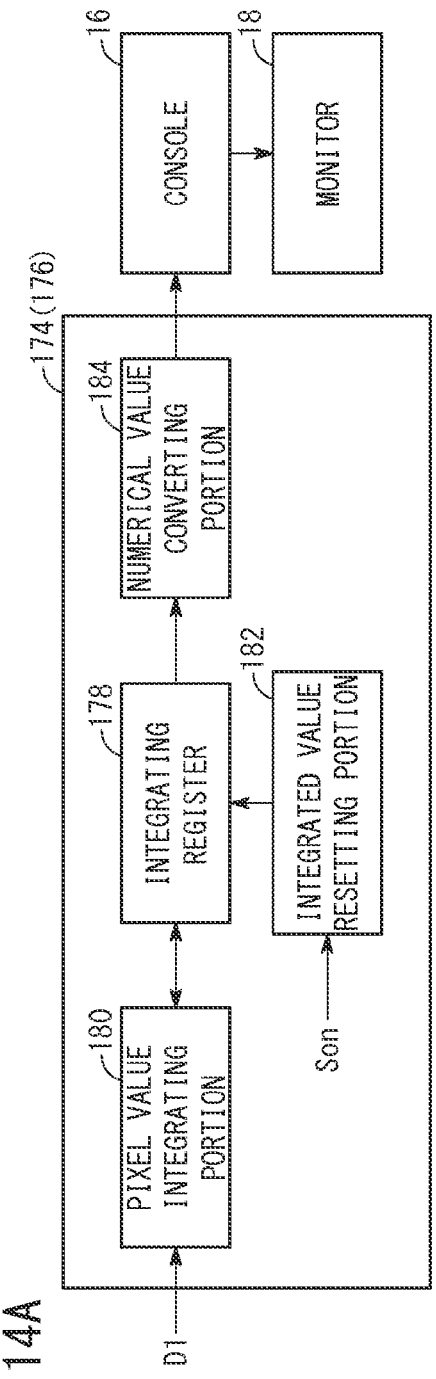
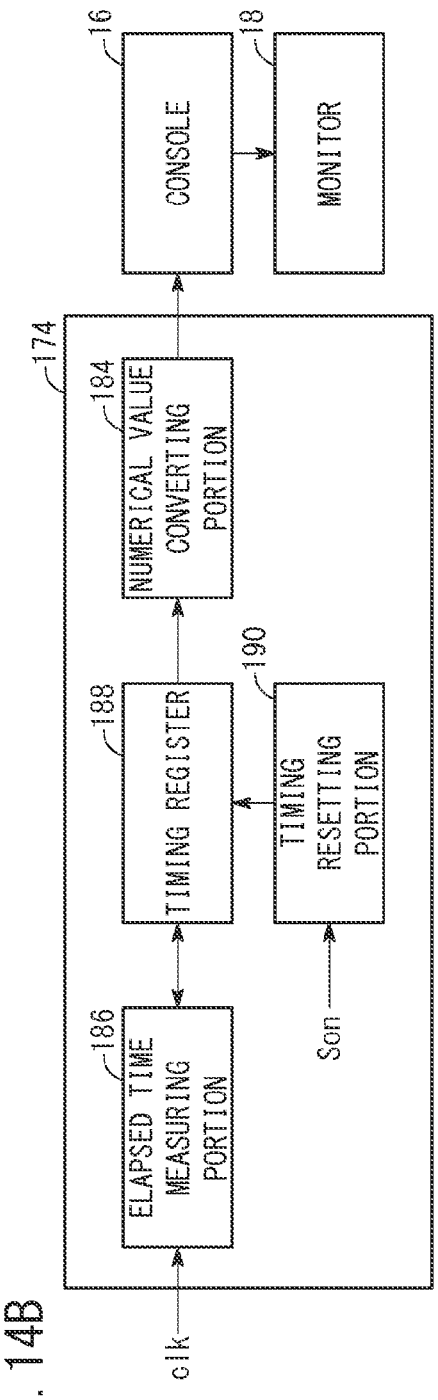
FIG. 14A
FIG. 14B

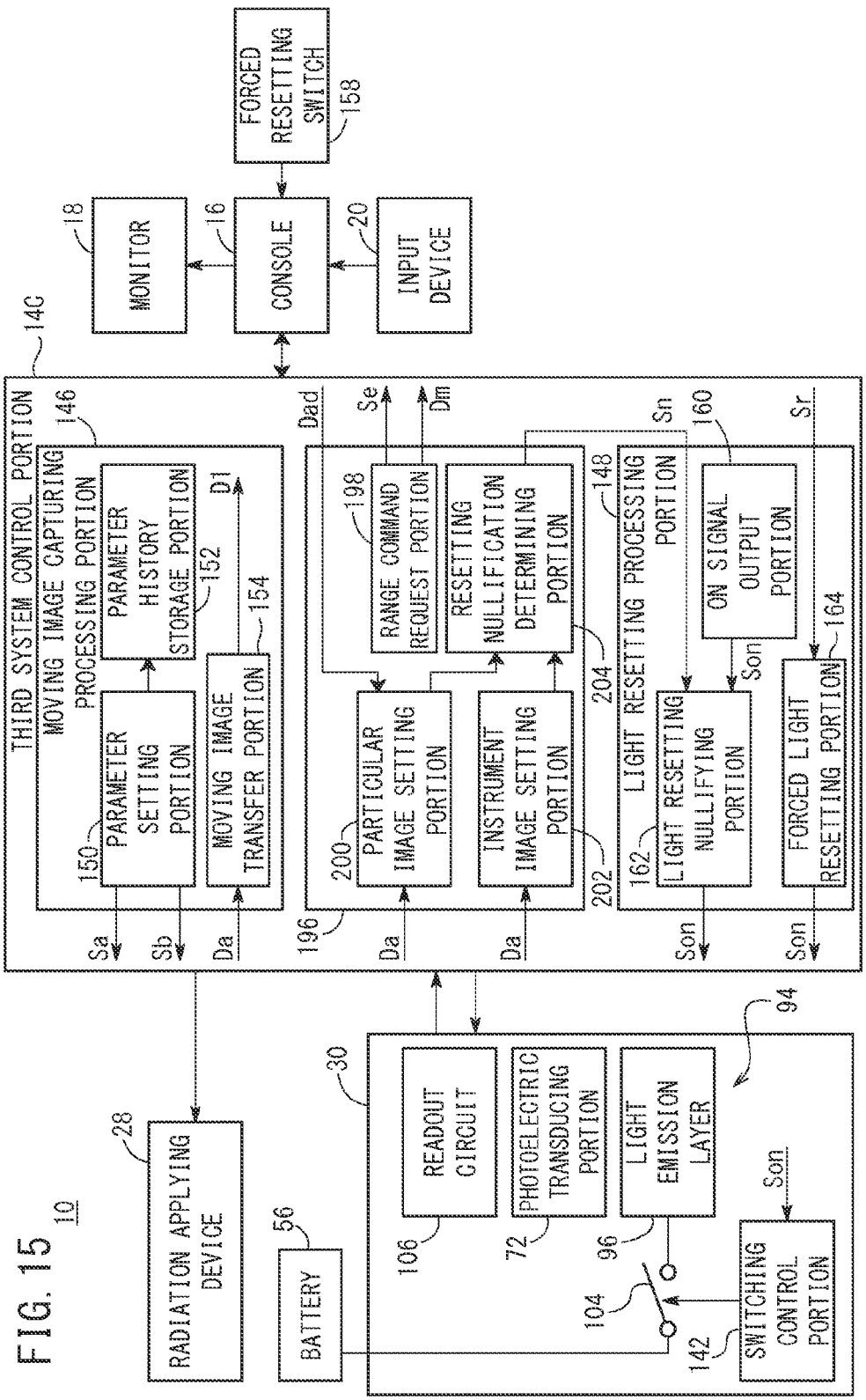

RADIATION IMAGE CAPTURING SYSTEM AND DETECTOR WITH RESET LIGHT CONTROL

CROSS-REFERENCE TO RELATED APPLICATIONS AND PRIORITY CLAIM

This application is a Continuation of International Application No. PCT/JP2012/076081 filed on Oct. 9, 2012, which was published under PCT Article 21(2) in Japanese, which is based upon and claims the benefit of priority from Japanese Patent Application No. 2011-234412 filed on Oct. 25, 2011, the contents all of which are incorporated herein by reference.

TECHNICAL FIELD

The present invention relates to a radiographic image (radiation image) capturing system having a radiation detecting device which includes a scintillator for converting radiation into fluorescence and a photoelectric converting portion for converting the fluorescence into an electric signal, and also to a radiation detecting device.

BACKGROUND ART

In the medical field, it has been widely practiced to apply radiation from a radiation source to a subject and detect the radiation that has passed through the subject with a radiation detecting device thereby to acquire a radiographic image of the subject (see, for example, Japanese Laid-Open Patent Publication No. 2006-140592).

Radiation detecting devices are roughly classified into indirect conversion radiation detecting devices which include a scintillator or the like for converting radiation into visible light and a photodiode or the like for converting the visible light into electric charges, and direct conversion radiation detecting devices which have a semiconductor material for directly absorbing and converting radiation into electric charges.

In a case where the above radiation detecting devices are used in high-speed moving image capturing processes such as fluorography and digital subtraction angiography (DSA) or the like, they may cause artifacts or afterimages due to the response of a phosphor (fluorophore) or a photoelectric transducer device, lowering the quality of generated images, immediately after X-rays of high dose are applied at one period of time or continuously.

One known solution to such afterimages is disclosed as an X-ray detector in Japanese Patent No. 4150079, for example. The X-ray detector disclosed in Japanese Patent No. 4150079 has a bias radiation source for irradiating a semiconductor device with an electromagnetic radiation thereby to prevent afterimages from being produced without complex corrective calculations. Specifically, it is known that it is effective to remove afterimages to apply resetting light to a photoelectric transducing portion, i.e., to reset the photoelectric transducing portion with light, which converts fluorescence generated by a scintillator into an electric signal.

SUMMARY OF INVENTION

However, once the photoelectric transducing portion is reset with light, the X-ray detector is unable to perform a radiographic moving image capturing process (fluorography) for a certain period of time that is equal to at least the sum of a period of time to apply the resetting light and a period of time to remove the effect of the applied resetting light, or even on the condition that the X-ray detector is able to perform a radiographic moving image capturing process, images generated in the radiographic moving image capturing process tend to be disrupted.

On the condition that the X-ray detector is incorporated in a radiographic image capturing system which allows the operator to recognize in real time how a catheter, for example, enters a subject, then a radiographic moving image capturing process may not be performed or captured images may be disrupted, posing an obstacle to the medical practice, in a case where the catheter should carefully be inserted into the subject.

The present invention has been made in view of the above drawbacks. It is an object of the present invention to provide a radiographic image capturing system and a radiation detecting device which are capable of selectively nullifying a light resetting process that is effective to remove afterimages thereby to avoid shortcomings resulting from the light resetting process.

Another object of the present invention is to provide a radiographic image capturing system and a radiation detecting device which are capable of preventing images from being disrupted by afterimages in a case where radiographic images need to be observed carefully, by forcibly resetting a photoelectric transducing portion with light in a situation where no obstacle will be posed to the medical practice.

[1] According to a first aspect of the present invention, there is provided a radiographic image capturing system comprising a radiographic image capturing apparatus including a radiation applying device having a radiation source and a radiation detecting device for converting radiation emitted from the radiation source and transmitted through a subject into a radiographic image and supplying the radiographic image, and a system control portion for controlling the radiographic image capturing apparatus to perform a radiographic image capturing process at a preset frame rate, wherein the radiation detecting device has a scintillator for converting the radiation into fluorescence, a photoelectric transducing portion for converting the fluorescence into an electric signal, and a resetting light source for irradiating the photoelectric transducing portion with resetting light, and the system control portion has a light resetting nullifying portion for nullifying application of the resetting light from the resetting light source in response to a resetting nullifying command.

[2] In the first aspect, the radiographic image capturing system may further comprise a resetting nullifying switch for supplying the resetting nullifying command in response to operator's input, wherein the light resetting nullifying portion may nullify the application of the resetting light from the resetting light source in response to the resetting nullifying command from the resetting nullifying switch.

[3] In the first aspect, the light resetting nullifying portion may nullify the application of the resetting light from the resetting light source only during a period in which the resetting nullifying command is supplied.

[4] In the first aspect, the system control portion may further include a resetting nullification commanding portion for supplying the resetting nullifying command based on a result of an analysis of the radiographic image from the radiation detecting device, and the light resetting nullifying portion may nullify the application of the resetting light from the resetting light source in response to the resetting nullifying command.

[5] The resetting nullification commanding portion may supply the resetting nullifying command based on a positional relationship between a designated particular image of the subject in the radiographic image from the radiation detecting device and an image of an instrument inserted in the subject.

[6] The resetting nullification commanding portion may supply the resetting nullifying command during a period in which the designated particular image of the subject and the image of the instrument inserted in the subject are in a preset positional relationship, and the light resetting nullifying portion may nullify the application of the resetting light from the resetting light source only during a period in which the resetting nullifying command is supplied.

[7] The preset positional relationship may be a relationship in which the image of the instrument has a portion placed in the particular image.

[8] In the first aspect, the radiographic image capturing system may further comprise a forced light resetting portion for forcibly applying the resetting light from the resetting light source in response to a forced resetting command.

[9] The radiographic image capturing system may further comprise a forced resetting switch for supplying the forced resetting command in response to operator's input, wherein the forced light resetting portion may forcibly apply the resetting light from the resetting light source in response to the forced resetting command from the forced resetting switch.

[10] The system control portion may further include a guidance output portion for providing guidance for turning on the forced resetting switch.

[11] The guidance may comprise an afterimage phenomenon in the radiographic image.

[12] The guidance output portion may include an accumulated dose calculating portion for calculating an accumulated dose that is stored in the radiation detecting device after the radiation detecting device has been irradiated with last resetting light, and the guidance output portion may supply the accumulated dose as representing the afterimage phenomenon in the radiographic image.

[13] The guidance may comprise an elapsed time from the application of last resetting light.

[14] The forced light resetting portion may forcibly apply the resetting light from the resetting light source in response to the forced resetting command supplied from an external source.

[15] The system control portion may further include a forced resetting commanding portion for supplying the forced resetting command based on the result of an analysis of the radiographic image from the radiation detecting device.

[16] The forced resetting commanding portion may supply the forced resetting command based on a positional relationship between a designated particular image of the subject in the radiographic image from the radiation detecting device and an image of an instrument inserted in the subject.

[17] The forced resetting commanding portion may include a motion vector calculating portion for determining a moving direction and a moving speed of the image of the instrument based on the plurality of radiographic images, and the forced resetting commanding portion may supply the forced resetting command in a case where the moving direction of the image of the instrument is oriented toward the particular image and before the image of the instrument reaches the particular image.

[18] The forced resetting commanding portion may supply the forced resetting command in a case where the moving direction of the image of the instrument is oriented toward the particular image and a time required until the image of the instrument reaches the particular image becomes a preset time.

[19] According to a second aspect of the present invention, there is provided a radiation detecting device comprising a scintillator for converting radiation into fluorescence, a photoelectric transducing portion for converting the fluorescence into an electric signal, a resetting light source for irradiating the photoelectric transducing portion with resetting light, and a light resetting nullifying portion for nullifying application of the resetting light from the resetting light source in response to a resetting nullifying command.

[20] In the second aspect, the radiation detecting device may further comprise a resetting nullifying switch for supplying the resetting nullifying command in response to operator's input, and the light resetting nullifying portion may nullify the application of the resetting light from the resetting light source in response to the resetting nullifying command from the resetting nullifying switch.

[21] The light resetting nullifying portion may nullify the application of the resetting light from the resetting light source only during a period in which the resetting nullifying command is supplied.

[22] In the second aspect, the light resetting nullifying portion may nullify the application of the resetting light from the resetting light source only during a period in which the resetting nullifying command is supplied from an external source.

[23] In the second aspect, the radiation detecting device may further comprise a forced light resetting portion for forcibly applying the resetting light from the resetting light source in response to a forced resetting command.

[24] The radiation detecting device may further comprise a forced resetting switch for supplying the forced resetting command in response to operator's input, and the forced light resetting portion may forcibly apply the resetting light from the resetting light source in response to the forced resetting command from the forced resetting switch.

[25] The radiation detecting device may further comprise a guidance output portion for providing guidance for turning on the forced resetting switch.

[26] The guidance may comprise an afterimage phenomenon in the radiographic image.

[27] The guidance output portion may include an accumulated dose calculating portion for calculating an accumulated dose that is stored in the radiation detecting device after application of last resetting light, and the guidance output portion may supply the accumulated dose as representing the afterimage phenomenon in the radiographic image.

[28] The guidance may comprise an elapsed time from the application of last resetting light.

[29] The forced light resetting portion may forcibly apply the resetting light from the resetting light source in response to the forced resetting command supplied from an external source.

The radiographic image capturing system and the radiation detecting device according to the present invention are capable of selectively nullifying a light resetting process that is effective to remove afterimages thereby to avoid shortcomings resulting from the light resetting process. Furthermore, the radiographic image capturing system and the radiation detecting device are capable of preventing images from being disrupted by afterimages in a case where radiographic images need to be observed carefully, by forcibly resetting a photoelectric transducing portion with light in a situation where no obstacle will be posed to the medical practice.

BRIEF DESCRIPTION OF DRAWINGS

FIG. 13 is a block diagram showing mainly the configuration of a second system control portion;

FIG. 14A is a block diagram showing the configuration of a guidance output portion according to a first principle;

FIG. 14B is a block diagram showing the configuration of a guidance output portion according to a second principle;

FIG. 15 is a block diagram showing mainly the configuration of a third system control portion;

DESCRIPTION OF EMBODIMENTS

Radiation detecting devices and radiographic image capturing systems according to embodiments of the present invention will be described below with reference to FIGS. 1 through 18.

Figure 1:
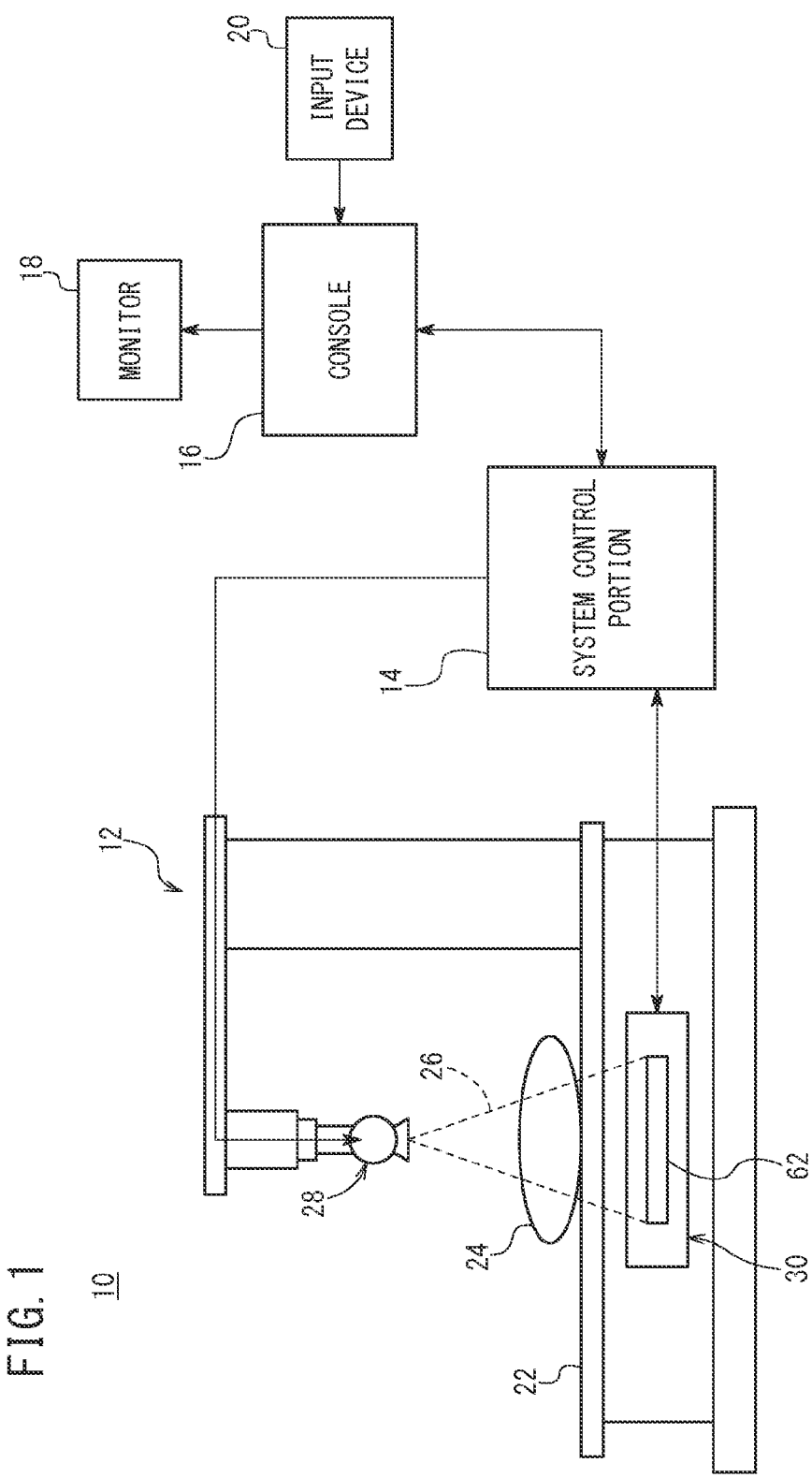
FIG. 1 is a view of a radiographic image capturing system according to an embodiment of the present invention.

As shown in FIG. 1, a radiographic image capturing system 10 according to an embodiment of the present invention has a radiographic image capturing apparatus 12 and a system control portion 14 for controlling the radiographic image capturing apparatus 12 to capture radiographic images at a preset frame rate which may be in the range from 15 frames per second to 60 frames per second, for example. The system control portion 14 is connected to a console 16 for data communication therewith. The console 16 is connected to a monitor 18 for observing images and diagnosing images, and an input device 20 such as a keyboard, a mouse, etc. for entering operator's input. The operator of the radiographic image capturing system 10, such as a doctor or a radiologist, sets a suitable irradiation energy level of radiation, which includes a tube voltage, a tube current, an irradiation time, etc., and a suitable frame rate for capturing images, to current conditions using the input device 20 for surgical operations and catheter inserting processes to be performed while viewing moving images. Data that are entered using the input device 20 and data generated and edited using the console 16 are supplied to the system control portion 14. Radiographic images that are captured are supplied from the system control portion 14 to the console 16, which displays the supplied radiographic images on the monitor 18.

The radiographic image capturing apparatus 12 has a radiation applying device 28 for applying radiation 26 with the preset irradiation energy level to a subject 24 on an image capturing table 22, and a radiation detecting device 30 for converting the radiation 26 that has passed through the subject 24 into a radiographic image and supplying the radiographic image to the system control portion 14.

Figure 2:
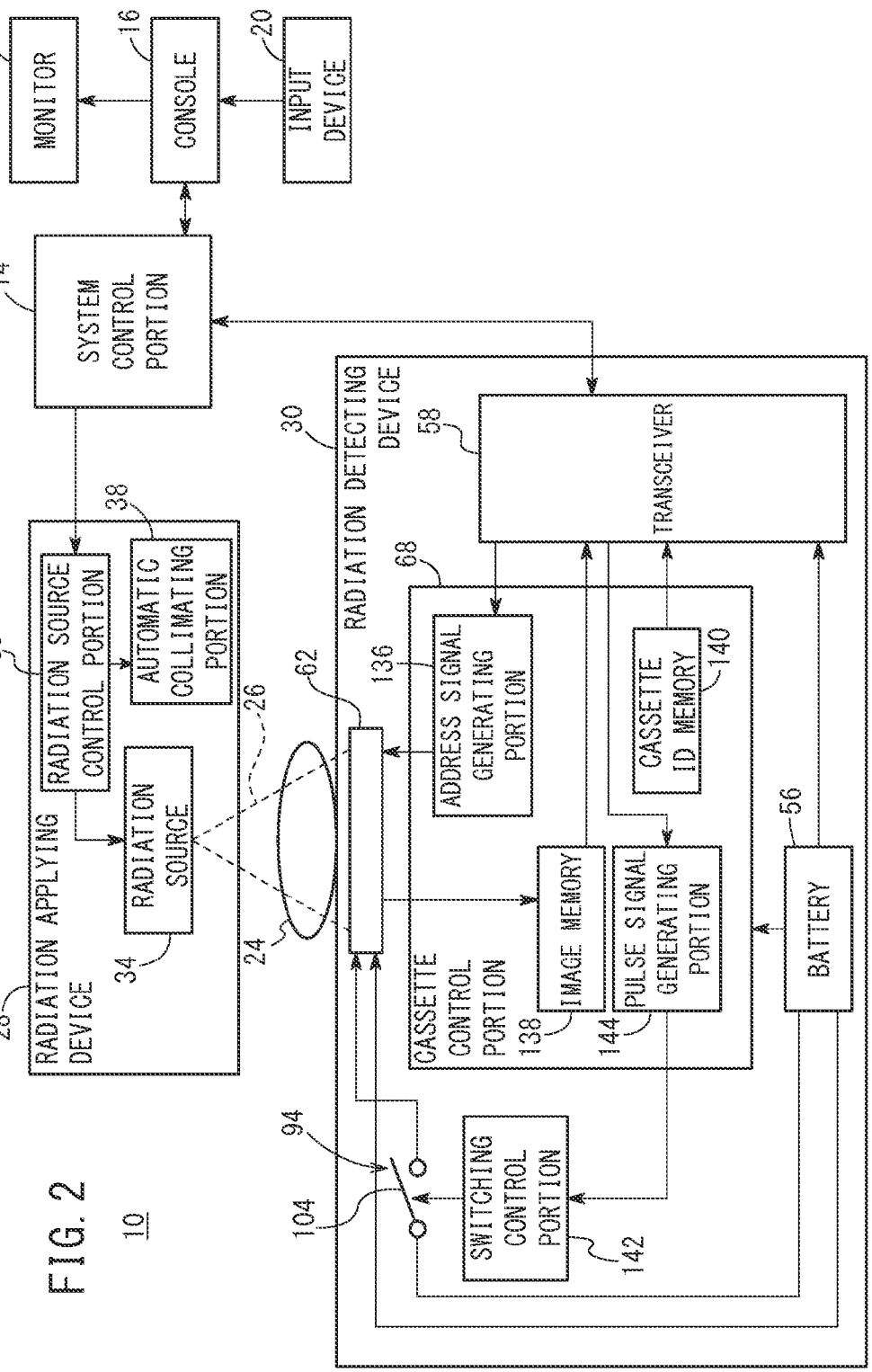
FIG. 2 is a block diagram showing mainly the configurations of a radiation applying device and a radiation detecting device.

As shown in FIG. 2, the radiation applying device 28 includes a radiation source 34, a radiation source control portion 36 for controlling the radiation source 34 based on commands from the system control portion 14, and an automatic collimating portion 38 for increasing or reducing an area that is irradiated with the radiation 26 based on commands from the system control portion 14.

Figure 3:
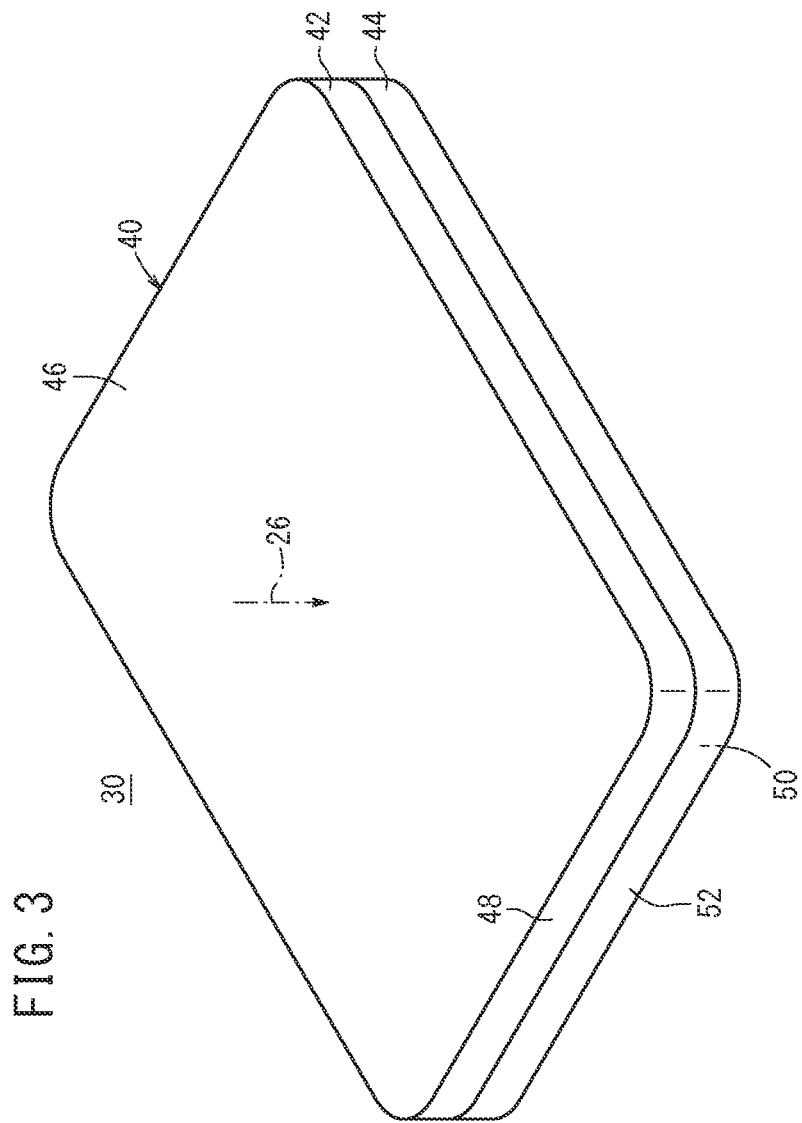
FIG. 3 is a perspective view of the radiation detecting device.
Figure 4:
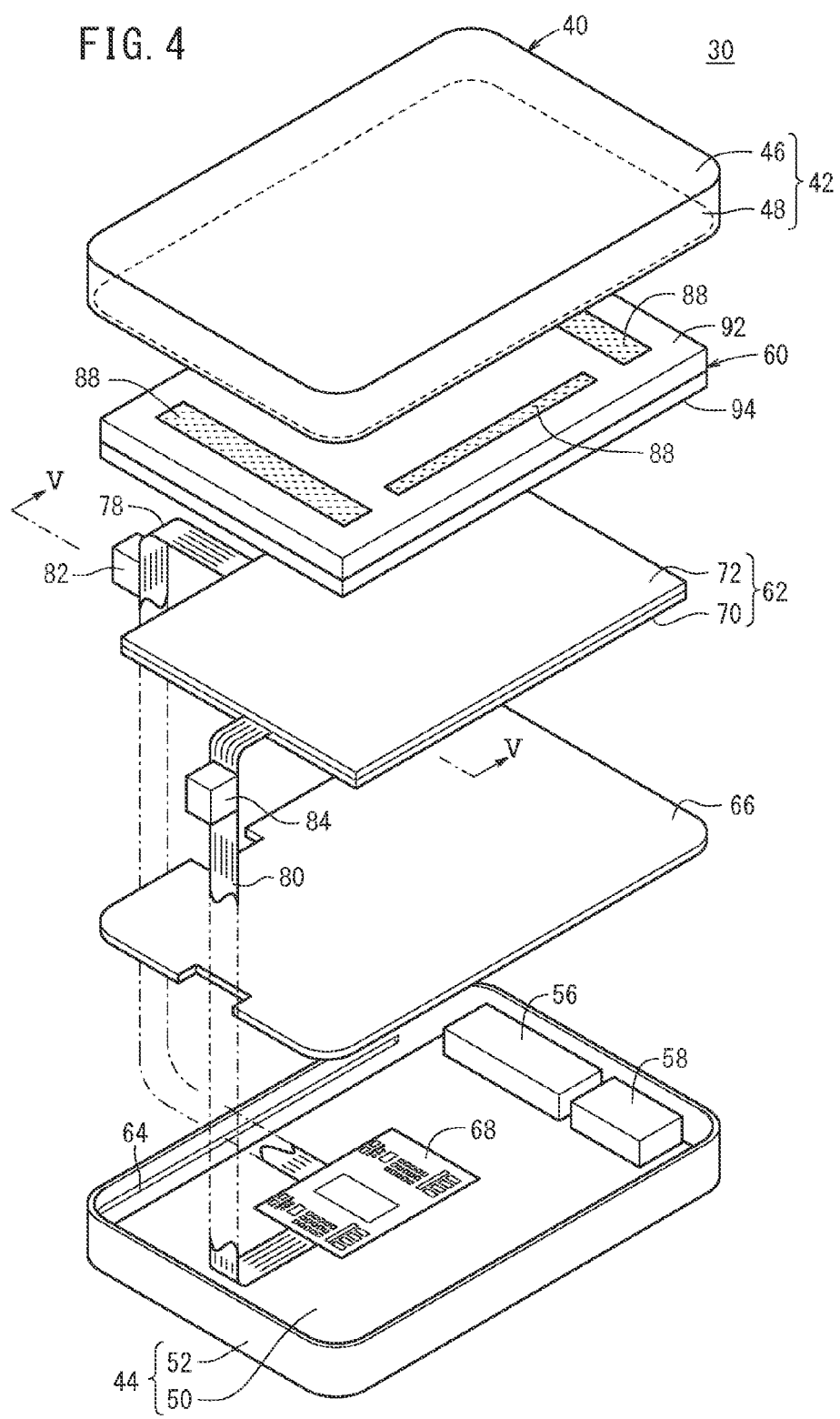
FIG. 4 is an exploded perspective view of the radiation detecting device.
Figure 5:
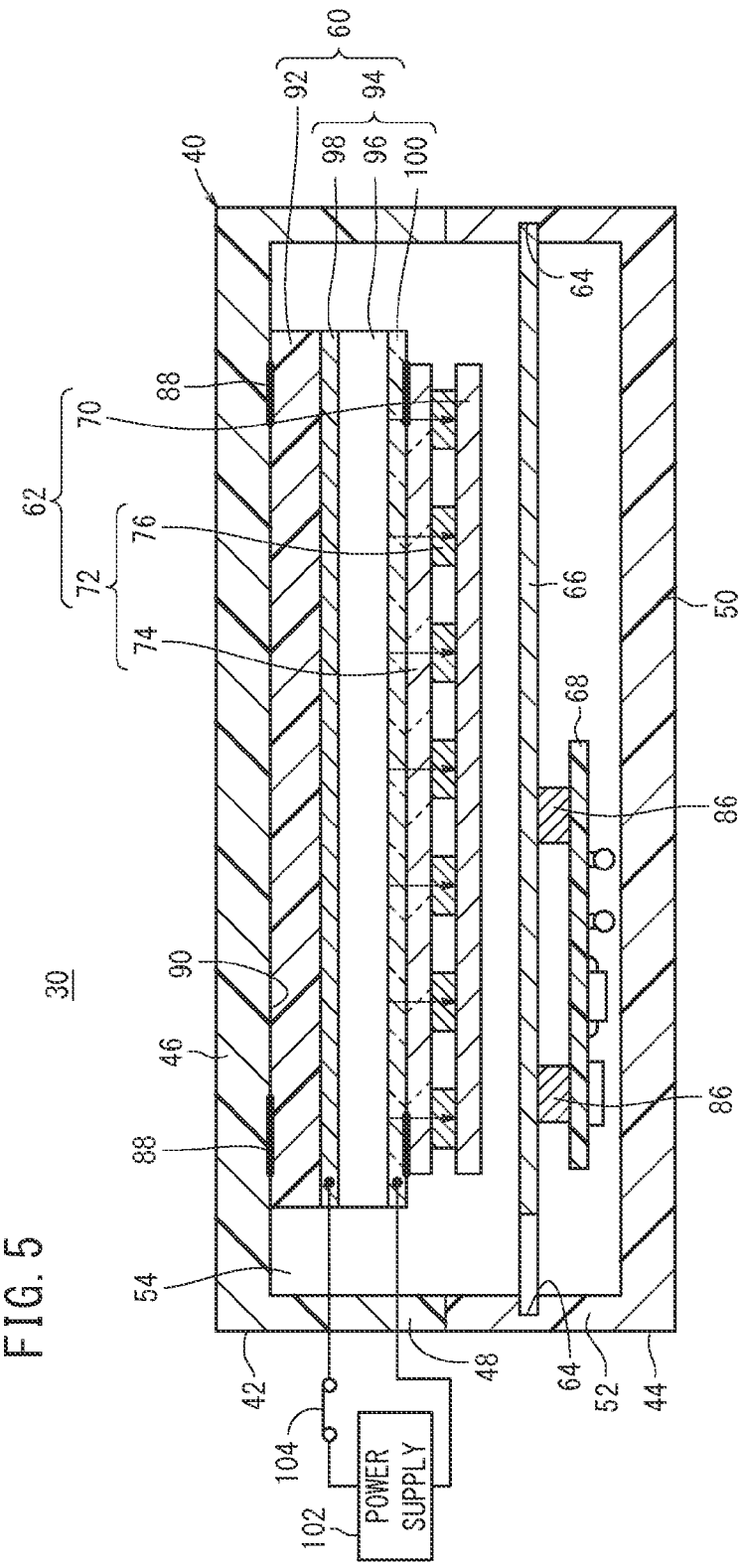
FIG. 5 is a cross-sectional view taken along line V-V of FIG. 4.

As shown in FIGS. 3 through 5, the radiation detecting device 30 has a casing 40 made of a material permeable to the radiation 26. The casing 40 comprises a first case 42 and a second case 44. The first case 42 has a first flat plate 46, which is of a substantially rectangular shape as viewed in plan, for being irradiated with the radiation 26, and a first side wall 48 extending around the peripheral edges of the first flat plate 46. The second case 44 has a second flat plate 50, which is similar in shape to the first flat plate 46, and a second side wall 52 erected on the peripheral edges of the second flat plate 50.

The first case 42 is detachably mounted on the second case 44. With the first case 42 mounted on the second case 44, the casing 40 defines a closed space 54 (see FIG. 5) therein.

Each of the first case 42 and the second case 44 of the casing 40 is made of a composite material such as carbon-fiber-reinforced plastics (CFRP) or the like, engineering plastics, a biomass material, aluminum, aluminum alloy, magnesium, magnesium alloy, or resin for reducing the overall weight of the radiation detecting device 30. The first case 42 and the second case 44 may be made of the same material or different materials. In FIG. 5, each of the first case 42 and the second case 44 is made as an integral case of CFRP.

The casing 40 houses therein a battery 56 as a power supply of the radiation detecting device 30, a transceiver 58 for sending signals including radiographic images to the system control portion 14 and receiving signals including radiographic images from the system control portion 14, a radiation detecting panel 62, which is of a rectangular shape as viewed in plan, supported by the first flat plate 46 with an intermediate member 60, to be described later, interposed therebetween, a shield plate 66 having edges disposed in a mounting groove 64 defined in an inner surface of the second side wall 52, and a cassette control portion 68 disposed between the shield plate 66 and the second flat plate 50, for controlling the radiation detecting panel 62.

The battery 56 supplies electric energy to the transceiver 58, the radiation detecting panel 62, and the cassette control portion 68. Lead plates that serve as shield plates, not shown, should desirably be disposed between the battery 56 and the first flat plate 46 and between the transceiver 58 and the first flat plate 46. The lead plates thus positioned are effective to prevent the battery 56 and the transceiver 58 from being unduly deteriorated by the radiation 26.

The radiation detecting panel 62 may comprise an indirect-conversion-type radiation detecting panel 62, which may be of the ISS (Irradiation Side Sampling) type or the PSS (Penetration Side Sampling) type, for converting the radiation 26 that has passed through the subject 24 into visible light (fluorescence) using a scintillator 70 and then converting the visible light into an analog electric signal using a photoelectric transducing portion 72.

In a case where the radiation detecting panel 62 is of the ISS type, then the photoelectric transducing portion 72 and the scintillator 70 are arranged successively along the direction in which the radiation 26 is applied. In a case where the radiation detecting panel 62 is of the PSS type, then the scintillator 70 and the photoelectric transducing portion 72 are arranged successively along the direction in which the radiation 26 is applied.

According to the present embodiment, the radiation detecting panel 62 is of the ISS type. Usually, the scintillator 70 emits more intensive light from its surface irradiated with the radiation 26 than the reverse side thereof. Therefore, the radiation detecting panel 62 of the ISS type has a shorter distance that the light emitted by the scintillator 70 travels before reaching the photoelectric transducing portion 72 than the radiation detecting panel of the PSS type. As the light is less liable to be scattered and dissipated, radiographic images are of a higher resolution.

The radiation detecting panel 62 may alternatively comprise a direct-conversion-type radiation detecting panel, instead of an indirect-conversion-type radiation detecting panel for directly converting the dose of the radiation 26 into an electric signal using solid-state detector elements made of amorphous selenium (a-Se).

The scintillator 70 is formed by evaporating a columnar crystalline structure of cesium iodide (CsI:Tl), for example, on a base plate according to a vacuum evaporation process. The scintillator 70 thus formed is capable of efficiently detecting the radiation 26 for generating radiographic images of a higher resolution.

Alternatively, the scintillator 70 may be formed by evaporating GOS ($Gd_2O_2S$:Tb), for example, on a base plate. The scintillator 70 thus formed is capable of converting the radiation 26 into visible light. The base plate may be made of CFRP, aluminum, aluminum alloy, magnesium, magnesium alloy, or resin.

The photoelectric transducing portion 72 is layered on a surface of the scintillator 70 which is closer to the first flat plate 46. The photoelectric transducing portion 72 comprises a flexible board 74 having a matrix of thin-film transistors (TFTs) made of an oxide semiconductor (IGZO) and a plurality of solid-state detector elements 76 (pixels) of amorphous silicon (a-Si) disposed on the array of TFTs.

Since the oxide semiconductor (IGZO) is selectively sensitive to only wavelengths shorter than 460 nm, it is effective to prevent switching noise from being generated by the light emitted from the scintillator 70.

The photoelectric transducing portion 72 and the cassette control portion 68 are electrically connected to each other by flexible cables 78, 80. The flexible cable 78 has a gate IC 82 for energizing the TFTs based on signals from the cassette control portion 68. The flexible cable 80 has an ASIC 84 (Application Specific Integrated Circuit) for amplifying analog electric signals from the solid-state detector elements 76 and converting the analog electric signals into digital electric signals. The flexible cable 78 is removably connected to a longitudinally extending side edge of the photoelectric transducing portion 72, and the flexible cable 80 is removably connected to a transversely extending side edge of the photoelectric transducing portion 72.

The shield plate 66 is made of a material, e.g., lead, for absorbing back scattered rays from the radiation detecting panel 62. Therefore, back scattered rays from the radiation detecting panel 62 are prevented from being applied to the cassette control portion 68 and hence preventing the cassette control portion 68 from deteriorating. The cassette control portion 68 is supported on the shield plate 66 by a plurality of brackets 86 (see FIG. 5).

The intermediate member 60, which is in the form of a plate, is disposed between the first flat plate 46 and the radiation detecting panel 62. The intermediate member 60 has a main intermediate member body 92 bonded to an inner irradiation surface 90 by an adhesive member 88 and a resetting light source 94.

The resetting light source 94 has a light emission layer 96, which is of a rectangular shape as viewed in plan, for emitting resetting light, a metal electrode 98 interposed between the light emission layer 96 and the main intermediate member body 92, a transparent electrode 100 interposed between the light emission layer 96 and the radiation detecting panel 62, for passing the resetting light therethrough, and a power supply 102 and a switch 104 that are electrically connected to the transparent electrode 100 and the metal electrode 98, respectively. The battery 56 may double as the power supply 102, or the power supply 102 may be a dedicated power supply separate from the battery 56.

The light emission layer 96 is made of an organic electroluminescent (EL) material or an inorganic EL material. The metal electrode 98 should preferably be made of a material having a high transmittance for the radiation 26 and a high reflectance for the resetting light. For example, the metal electrode 98 may be made of aluminum or the like, for example. The transparent electrode 100 may be made of ITO or the like, for example.

According to the present embodiment, the cassette control portion 68 controls the power supply 102 and the switch 104 of the resetting light source 94 to cause the light emission layer 96 to emit resetting light prior to a radiographic image capturing process.

By way of example, the photoelectric transducing portion 72 of the radiation detecting panel 62, which is of the indirect conversion type, and a readout circuit 106 for the photoelectric transducing portion 72 will be described in detail below with reference to FIG. 6.

The photoelectric transducing portion 72 has a photoelectric transducing layer 108 including the pixels 76 made of a-Si or the like for converting visible light into an electric signal and disposed on an array of thin-film transistors (TFTs) 110 arranged in rows and columns. Each of the pixels 76 stores an electric charge generated in a case where visible light is converted into an analog electric signal. The electric charges stored in the pixels 76 can be read as an image signal in a case where the TFTs 110 are turned on in the successive rows.

The readout circuit 106 has the TFTs 110 connected to the respective pixels 76, gate lines 112 connected to the TFTs 110 and extending parallel to the rows of the TFTs 110, and signal lines 114 connected to the columns of the TFTs 110 and extending parallel to the columns of the TFTs 110. The gate lines 112 are connected to a line scanning driver 116, whereas the signal lines 114 are connected to a multiplexer 118. The gate lines 112 are supplied with control signals Von, Voff for turning on and off the TFTs 110 along the rows from the line scanning driver 116. The line scanning driver 116 includes a plurality of switches SW1 for switching between the gate lines 112 and a first address decoder 120 for supplying a selection signal for selecting one of the switches SW1. The first address decoder 120 is supplied with an address signal from the cassette control portion 68.

The signal lines 114 are supplied with electric charges stored by the pixels 76 through the TFTs 110 arranged in the columns. The electric charges supplied to the signal lines 114 are amplified by charge amplifiers 122. The charge amplifiers 122 are connected through respective sample and hold circuits 124 to the multiplexer 118.

The electric charges read out from the columns are supplied through the signal lines 114 to the charge amplifiers 122 corresponding to the columns. Each of the charge amplifiers 122 comprises an operational amplifier 126, a capacitor 128, and a switch 130. In a case where the switch 130 is turned off, the charge amplifier 122 converts an electric charge signal applied to an input terminal of the operational amplifier 126 into a voltage signal, and outputs the voltage signal. The charge amplifier 122 amplifies the electric charge signal with a gain set by the cassette control portion 68. Information (gain setting information) about the gain for the charge amplifier 122 is supplied from the system control portion 14 to the cassette control portion 68, which sets the gain for the charge amplifier 122 based on the supplied gain setting information.

The operational amplifiers 126 have other input terminals grounded, i.e., connected to ground potential (GND). In a case where all the TFTs 110 are turned on and the switches 130 are turned on, the electric charges stored in the capacitors 128 are discharged by closed circuits of the capacitors 128 and the switches 130, and the electric charges stored in the pixels 76 are drained (swept out) to ground potential (GND) through the switches 130 and the operational amplifiers 126. The process of discharging the electric charges stored in the capacitors 128 and draining the electric charges stored in the pixels 76 to ground potential (GND) by turning on the switches 130 of the charge amplifiers 122 is referred to as a resetting process (dummy reading process). In particular, a process of draining the electric charges stored in all the pixels to ground potential is referred to as "all-pixel resetting process". In the resetting process, voltage signals that correspond to the electric charge signals stored in the pixels 76 are not supplied to the multiplexer 118, but drained.

The multiplexer 118 includes a plurality of switches SW2 for successively switching between the signal lines 114 and a second address decoder 132 for supplying a selection signal for selecting one of the switches SW2. The second address decoder 132 is supplied with an address signal from the cassette control portion 68. The multiplexer 118 has an output terminal connected to an A/D converter 134. A radiographic image signal is converted by the A/D converter 134 into a digital image signal representing radiographic image information, which is supplied to the cassette control portion 68.

The TFTs 110 which function as switching devices may be combined with another image capturing device such as a CMOS (Complementary Metal-Oxide Semiconductor) image sensor or the like. Alternatively, the TFTs 110 may be replaced with a CCD (Charge-Coupled Device) image sensor for shifting and transferring electric charges with shift pulses which correspond to gate signals in the TFTs.

As shown in FIG. 2, the cassette control portion 68 of the radiation detecting device 30 includes an address signal generating portion 136 for the readout circuit 106 (see FIG. 6), an image memory 138, and a cassette ID memory 140.

Figure 6:
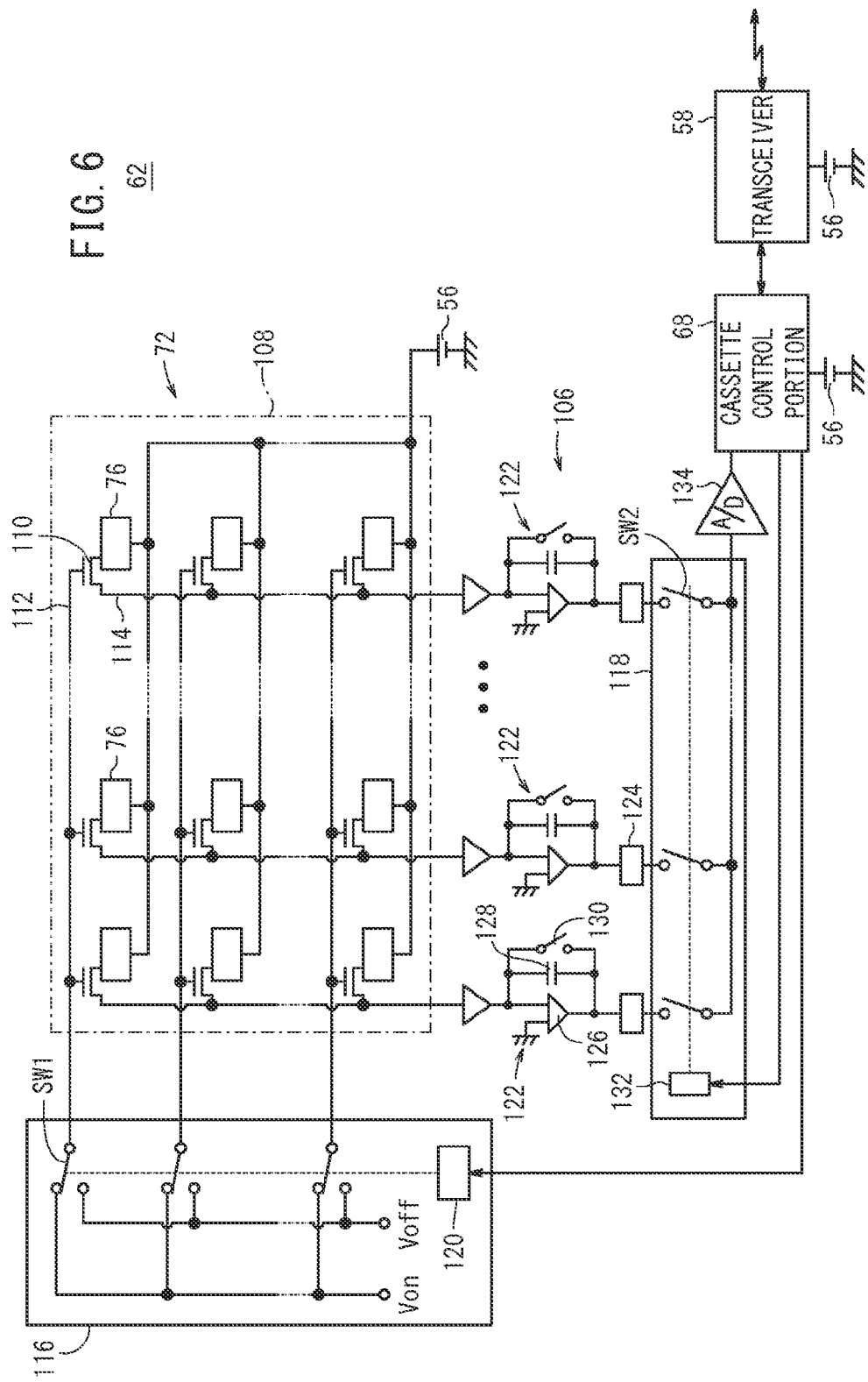
FIG. 6 is a circuit diagram showing mainly a photoelectric transducing portion and a readout circuit.

The address signal generating portion 136 supplies address signals to the first address decoder 120 of the line scanning driver 116 and the second address decoder 132 of the multiplexer 118 of the readout circuit 106 shown in FIG. 6 based on readout control information for radiographic images from the system control portion 14, for example. The readout control information includes information representing a progressive mode, an interlace mode (an odd-numbered row readout mode, an even-numbered row readout mode, an every third row readout mode, an every fourth row readout mode, etc.), and a binning mode (a 4-pixels-into-1 readout mode, a 6-pixels-into-1 readout mode, a 9-pixels-into-1 readout mode, etc.). In the 4-pixels-into-1 readout mode, for example, two adjacent gate lines 112 are simultaneously energized, i.e., supplied with the control signal Von, and two adjacent signal lines 114 are simultaneously energized, thereby mixing electric charges in four adjacent pixels in two rows and two columns into a single superpixel electric charge to be read. The address signal generating portion 136 generates address signals depending on a mode represented by the readout control information, and supplies the generated address signals to the first address decoder 120 of the line scanning driver 116 and the second address decoder 132 of the multiplexer 118. The readout control information is generated by the system control portion 14 based on input entered by the operator, for example, and supplied to the cassette control portion 68 of the radiation detecting device 30.

The readout control information supplied from the system control portion 14 includes, in addition to the information about the readout modes (readout mode information) described above, image capturing range information for designating an image capturing range. For example, on the condition that the operator sets an image capturing range for moving images using the input device 20 and the monitor 18, then the image capturing range information includes the addresses of the gate lines 112 and the addresses of the signal lines 114 included in the image capturing range thus set. The image capturing range information may include start addresses (numbers) and end addresses (numbers) of the gate lines 112 and start addresses (numbers) and end addresses (numbers) of the signal lines 114 included in the image capturing range. On the condition that the readout mode information represents an odd-numbered row readout mode (decimating or thinning mode), for example, then odd-numbered gate lines 112 among the gate lines 112 included in the image capturing range of the radiation detecting panel 62 are successively selected, and signal electric charges from the signal lines 114 included in the image capturing range of the radiation detecting panel 62 are not combined, but successively transferred to the A/D converter 134. On the condition that the readout mode information represents a 4-pixels-into-1 readout mode (binning mode), for example, then two at a time of the gate lines 112 included in the image capturing range are successively selected, and signal electric charges from adjacent two of the signal lines 114 included in the image capturing range are combined, i.e., signal electric charges from four pixels are combined, and successively transferred to the A/D converter 134.

The image memory 138 stores radiographic image information from the readout circuit 106. The cassette ID memory 140 stores cassette ID information for identifying the radiation detecting device 30.

The transceiver 58 sends the cassette ID information stored in the cassette ID memory 140 and the radiographic image information stored in the image memory 138 to the system control portion 14 via a wired communication link or a wireless communication link.

The radiation detecting device 30 has a switching control portion 142 for turning on and off the switch 104 of the resetting light source 94. The cassette control portion 68 includes a pulse signal generating portion 144. The pulse signal generating portion 144 generates a pulse signal having a certain pulse duration in response to an ON signal, i.e., a signal for performing a light resetting process, from the system control portion 14, and supplies the generated pulse signal to the switching control portion 142. Based on the supplied pulse signal, the switching control portion 142 turns on the switch 104 for the pulse duration of the pulse signal. The light emission layer 96 now emits resetting light for a period of time that corresponds to the pulse duration, and the emitted resetting light is applied to the photoelectric transducing portion 72, thereby performing the light resetting process.

Specific examples of the system control portion 14 of the radiographic image capturing system 10 will be described below with reference to FIGS. 7 through 17.

Figure 7:
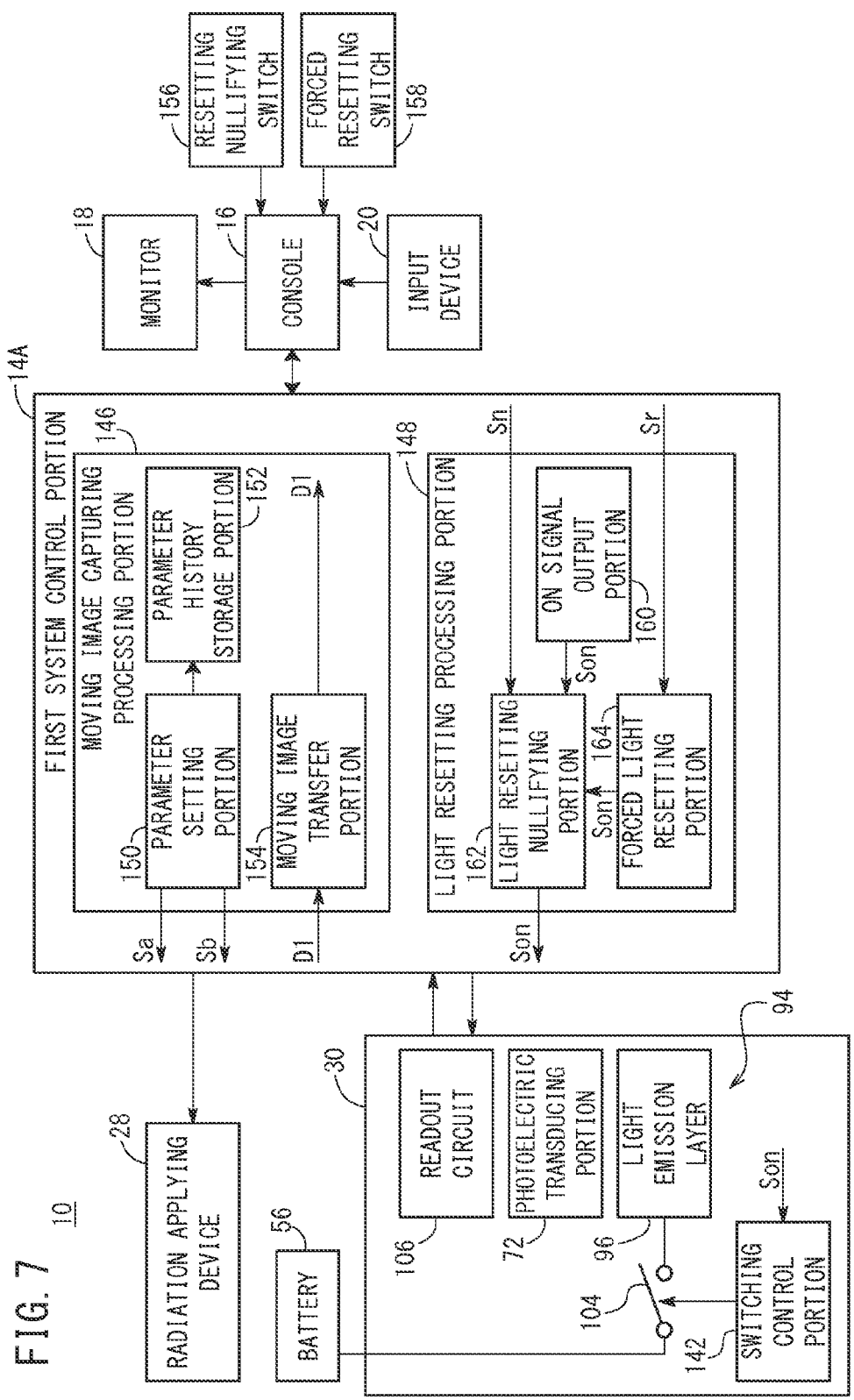
FIG. 7 is a block diagram showing mainly the configuration of a first system control portion.

As shown in FIG. 7, a system control portion according to a first specific example (hereinafter referred to as "first system control portion 14A) has a moving image capturing processing portion 146 and a light resetting processing portion 148.

The moving image capturing processing portion 146 has a parameter setting portion 150, a parameter history storage portion 152, and a moving image transfer portion 154.

In a case where new parameters including an irradiation energy level, a frame rate, or the like are set based on input from the operator, the parameter setting portion 150 stores them as latest parameters including newly set irradiation energy level, a frame rate, or the like in the parameter history storage portion 152. Particularly, in a case where a new irradiation energy level is set, the parameter setting portion 150 supplies irradiation energy level setting information Sa including information about the new irradiation energy level, i.e., information of a tube voltage, a tube current, an irradiation time, etc., to the radiation applying device 28. On the condition that a gain of the charge amplifiers 122 or a readout mode is newly set, then the parameter setting portion 150 supplies readout control information Sb including information about the newly set gain or readout mode to the radiation detecting device 30.

The parameter history storage portion 152 stores irradiation energy levels and frame rates (and the like) that were set over a predetermined period in the past from the present, of the irradiation energy levels and the frame rates (and the like) which have been set so far.

The moving image transfer portion 154 receives radiographic images Da successively supplied from the radiation detecting device 30, and transfers the received radiographic images Da to the console 16. The console 16 displays the successively transferred radiographic images Da on the monitor 18. The monitor 18 thus displays the radiographic images Da as a moving image.

A resetting nullifying switch 156 and a forced resetting switch 158 are connected to the console 16. In a case where the operator turns on the resetting nullifying switch 156, it generates a resetting nullifying command signal Sn which is, e.g., high in level over a period during which the operator turns on the resetting nullifying switch 156. The resetting nullifying command signal Sn is supplied from the resetting nullifying switch 156 through the console 16 to the first system control portion 14A. In a case where the operator turns on the forced resetting switch 158, it generates a forced resetting command signal Sr having a certain pulse duration. The forced resetting command signal Sr is supplied from the forced resetting switch 158 through the console 16 to the first system control portion 14A.

The light resetting processing portion 148 has an ON signal output portion 160, a light resetting nullifying portion 162, and a forced light resetting portion 164.

The ON signal output portion 160 generates an ON signal Son at the selected frame interval in the range from 5 to 100 frames, for example, based on the latest frame rate stored in the parameter history storage portion 152. For example, on the condition that the interval of 50 frames is selected, then the ON signal output portion 160 generates an ON signal Son at the frame interval between the 50nth (n: 1, 2, 3, . . . ) frame and the 50nth+1 frame. In a case where the ON signal Son is supplied to the radiation detecting device 30, the light resetting process is performed on the radiation detecting device 30.

The forced light resetting portion 164 is supplied with a forced resetting command signal Sr from the forced resetting switch 158. In a case where the forced light resetting portion 164 is supplied with the forced resetting command signal Sr, the forced light resetting portion 164 generates an ON signal Son having the same attributes (pulse duration, amplitude) as the ON signal Son from the ON signal output portion 160.

The light resetting nullifying portion 162 is supplied with the ON signal Son from the ON signal output portion 160, the ON signal Son from the forced light resetting portion 164, and the resetting nullifying command signal Sn from the resetting nullifying switch 156. While the light resetting nullifying portion 162 is not being supplied with the resetting nullifying command signal Sn, the light resetting nullifying portion 162 supplies the ON signal Son from the ON signal output portion 160 and the ON signal Son from the forced light resetting portion 164. In a case where the light resetting nullifying portion 162 is supplied with the resetting nullifying command signal Sn, the light resetting nullifying portion 162 does not supply the ON signal Son from the ON signal output portion 160 and the ON signal Son from the forced light resetting portion 164. Normally, the light resetting process will be performed. However, during a period of time in which the light resetting nullifying portion 162 is supplied with the resetting nullifying command signal Sn, the light resetting nullifying portion 162 does not perform the light resetting process, i.e., nullifies the light resetting process.

Processing operation of the radiographic image capturing system 10 which has the first system control portion 14A will be described below with reference to FIGS. 8 through 12. The moving image capturing processing portion 146 and the light resetting processing portion 148 operate in a multitasking mode.

Figure 8:
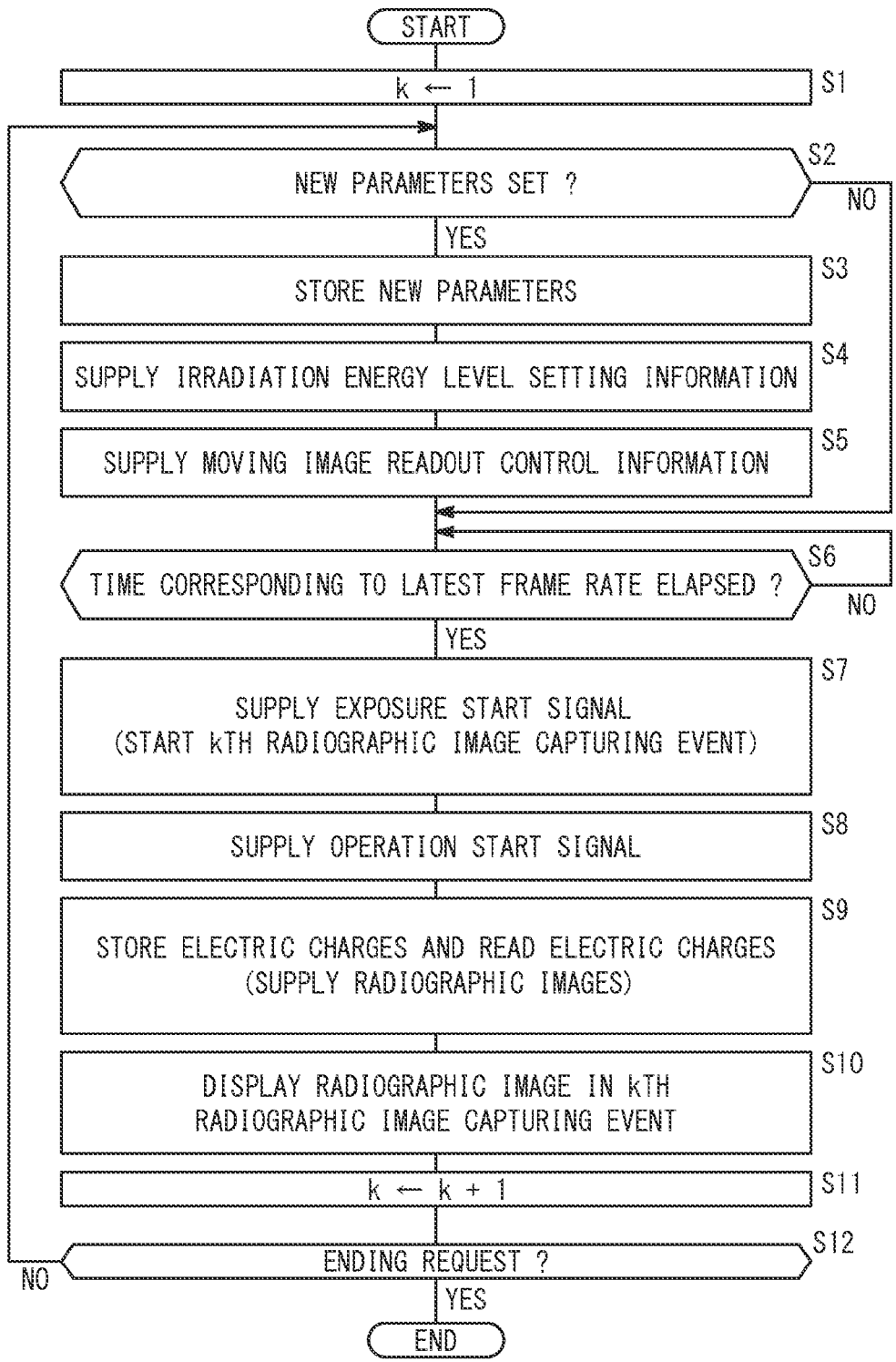
FIG. 8 is a flowchart of a processing sequence of a moving image capturing processing portion of the first system control portion.

First, a processing sequence of the moving image capturing processing portion 146 will be described below with reference to FIG. 8. In step S1 shown in FIG. 8, the first system control portion 14A stores an initial value (=1) in a counter k for counting image capturing events.

In step S2, the parameter setting portion 150 judges whether new parameters including an irradiation energy level, a frame rate, an image capturing range, and a readout mode, etc. for the radiation 26 has been set or not. On the condition that the operator has set new parameters, then control goes to step S3 in which the irradiation energy level, the frame rate, etc. that have been newly set are stored as latest parameters in the parameter history storage portion 152.

On the condition that an irradiation energy level has been newly set, then the parameter setting portion 150 supplies irradiation energy level setting information Sa including information about the newly set irradiation energy level, i.e., information of a tube voltage, a tube current, an irradiation time, etc., to the radiation applying device 28 in step S4. Based on the irradiation energy level setting information Sa from the first system control portion 14A, the radiation source control portion 36 of the radiation applying device 28 sets the irradiation energy level of the radiation 26 to be emitted from the radiation source 34 to the newly set irradiation energy level.

On the condition that an image capturing range and a readout mode, etc. have been newly set, then the parameter setting portion 150 supplies readout control information Sb including information about the newly set image capturing range and information about the newly set readout mode to the radiation detecting device 30 in step S5. The cassette control portion 68 of the radiation detecting device 30 supplies the readout control information Sb to the address signal generating portion 136.

In step S6, the first system control portion 14A judges whether a period of time corresponding to the latest frame rate Fr has elapsed from the start time of the preceding radiographic image capturing event or not. On the condition that the counter k indicates the initial value or the period of time corresponding to the latest frame rate Fr has elapsed from the starting time of the preceding radiographic image capturing event, then control goes to step S7. In step S7, the first system control portion 14A supplies an exposure start signal Sc (see FIG. 10) to the radiation applying device 28 at the start time of a kth radiographic image capturing event. Based on the exposure start signal Sc from the first system control portion 14A, the radiation source control portion 36 of the radiation applying device 28 controls the radiation source 34 to emit the radiation 26 at the set irradiation energy level.

In step S8, the first system control portion 14A supplies an operation start signal Sd (see FIG. 10) indicative of storage and readout of electric charges to the radiation detecting device 30.

In step S9, based on the operation start signal Sd from the first system control portion 14A, the radiation detecting device 30 stores and reads out electric charges. Specifically, the radiation 26 that has passed through the subject 24 is converted by the scintillator 70 of the photoelectric transducing portion 72 into visible light, which is then converted by the pixels 76 of the photoelectric transducing portion 72 into electric charges in amounts that depend on the intensity of the visible light. The electric charges are stored in the pixels 76.

In a next readout period, the address signal generating portion 136 generates address signals based on the supplied readout control information Sb (image capturing range information, readout mode information, etc.), and supplies the generated address signals to the first address decoder 120 of the line scanning driver 116 and the second address decoder 132 of the multiplexer 118 of the readout circuit 106. The readout circuit 106 reads the electric charges from the pixels 76 according to the readout control information Sb, and outputs the read electric charges as radiographic images Da, which will be displayed as a moving image, using the image memory 138 in an FIFO mode, for example. The radiographic images Da from the radiation detecting device 30 are supplied to the first system control portion 14A.

In step S10, the first system control portion 14A transfers the supplied radiographic images Da to the console 16. The console 16 stores the transferred radiographic images Da in a frame memory, and displays the radiographic image in the kth radiographic image capturing event as a radiographic image in a kth frame on the monitor 18.

In step S11, the first system control portion 14A updates the counter k by +1.

In step S12, the first system control portion 14A judges whether there is a request for ending the moving image capturing process or not. On the condition that there is not a request for ending the moving image capturing process, then control goes back to step S2 to repeat the processing from step S2. The monitor 18 now displays a radiographic moving image at the set frame rate. On the condition that there is a request for ending the moving image capturing process in step S12, then the moving image capturing process is ended.

Figure 9:
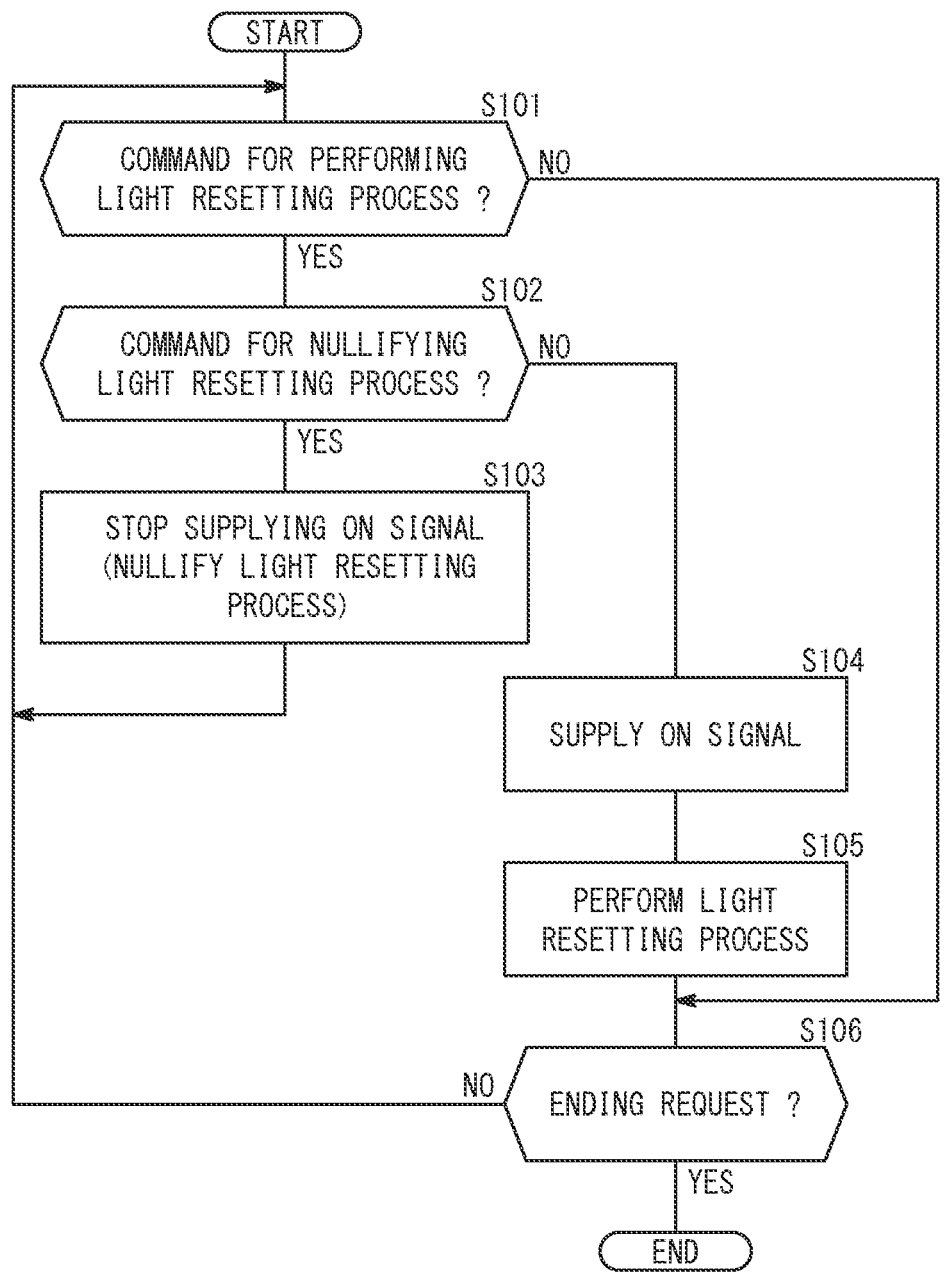
FIG. 9 is a flowchart of a processing sequence of a light resetting processing portion of the first system control portion.

A processing sequence of the light resetting processing portion 148 will be described below with reference to FIG. 9. In step S101 shown in FIG. 9, the light resetting nullifying portion 162 judges whether there is a command for performing the light resetting process or not. Specifically, the light resetting nullifying portion 162 judges whether it is supplied with an ON signal Son from the ON signal output portion 160 or the forced light resetting portion 164 or not. On the condition that the light resetting nullifying portion 162 is supplied with an ON signal Son, i.e., a command for performing the light resetting process, then control goes to step S102 in which the light resetting nullifying portion 162 judges whether there is a command for nullifying the light resetting process or not. Specifically, the light resetting nullifying portion 162 judges whether it is supplied with a resetting nullifying command signal Sn or not. On the condition that the light resetting nullifying portion 162 is supplied with a resetting nullifying command signal Sn, i.e., a command for nullifying the light resetting process, then control goes to step S103 in which the supply of the ON signal Son is stopped, nullifying the command for performing the light resetting process. Thereafter, control goes back to step S101 to repeat the processing from step S101.

In a case where the light resetting nullifying portion 162 judges that it is supplied with a command for performing the light resetting process in step S101 and on the condition that the light resetting nullifying portion 162 judges that it is not supplied with a command for nullifying the light resetting process in step S102, then control goes to step S104 in which the light resetting nullifying portion 162 supplies an ON signal Son for performing the light resetting process to the radiation detecting device 30. In step S105, the photoelectric transducing portion 72 is reset by being irradiated with resetting light.

On the condition that the light resetting nullifying portion 162 judges that it is not supplied with a command for performing the light resetting process in step S101 or on the condition that the light resetting process is performed in step S105, control goes to step S106. In step S106, the first system control portion 14A judges whether there is a request for ending the moving image capturing process or not. On the condition that there is not a request for ending the moving image capturing process, then control goes back to step S101 to repeat the light resetting process from step S101. On the condition that there is a request for ending the moving image capturing process in step S106, then the light resetting process is ended.

Figure 10:
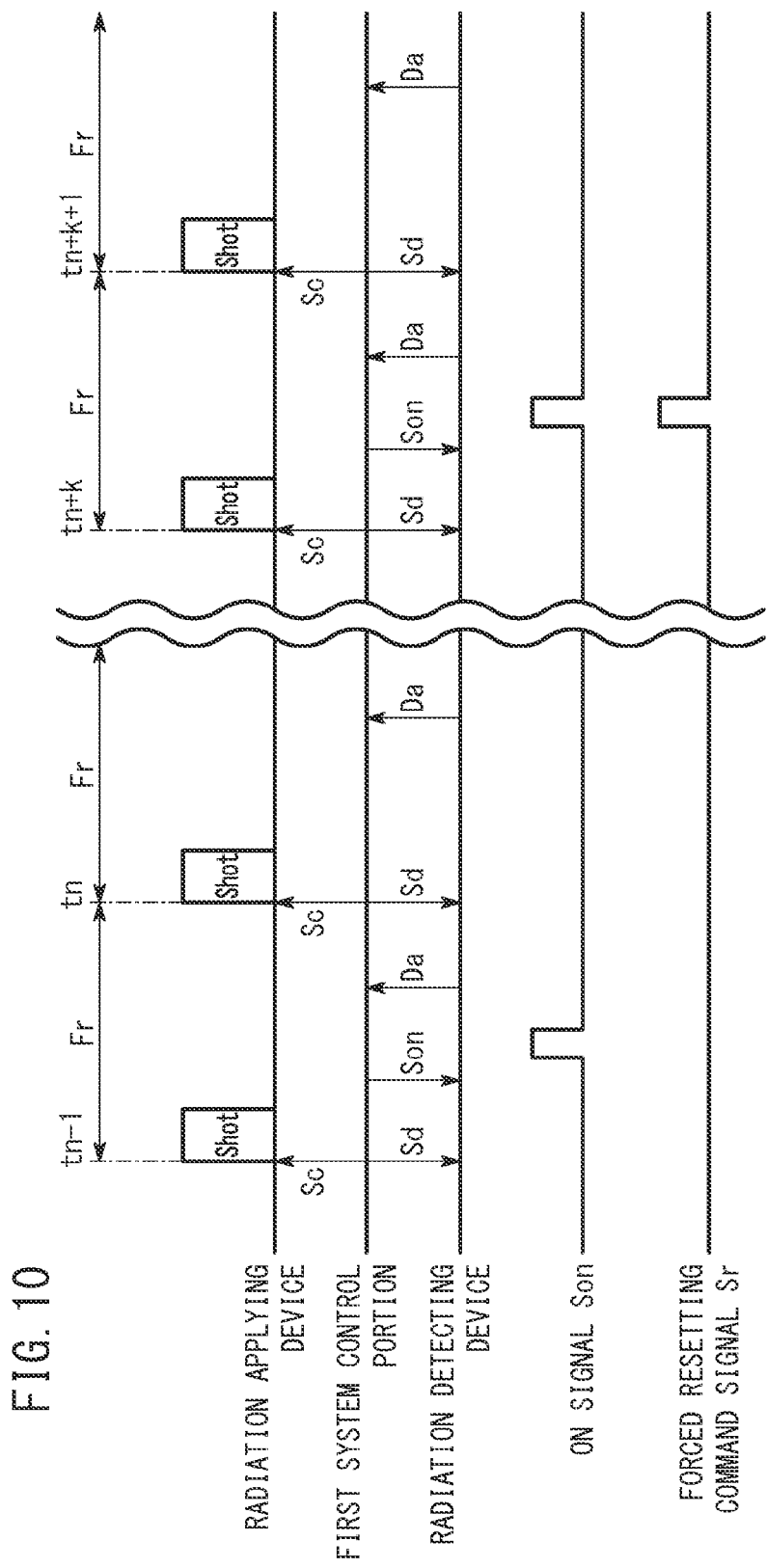
FIG. 10 is a timing chart of a processing sequence of the first system control portion, particularly including operation of a forced light resetting portion.

The processing sequences will be described below with reference to an example shown in FIG. 10. At start time tn−1 of an (N−1)th (N=2, 3, . . . ) radiographic image capturing event, the first system control portion 14A supplies an exposure start signal Sc to the radiation applying device 28 and also supplies an operation start signal Sd to the radiation detecting device 30, whereupon the first system control portion 14A is supplied with a radiographic image Da captured in the (N−1)th radiographic image capturing event. The first system control portion 14A transfers the supplied radiographic image Da to the console 16, which displays the radiographic image Da as a radiographic image in an (N−1)th frame on the monitor 18.

Similarly, at start time tn of an Nth radiographic image capturing event upon elapse of the latest frame rate Fr from the above start time tn−1, the first system control portion 14A supplies an exposure start signal Sc to the radiation applying device 28 and also supplies an operation start signal Sd to the radiation detecting device 30, whereupon the first system control portion 14A is supplied with a radiographic image Da captured in the Nth radiographic image capturing event. The first system control portion 14A transfers the radiographic image Da to the console 16, which displays the radiographic image Da as a radiographic image in an Nth frame on the monitor 18. The above processes are repeated to display a radiographic moving image on the monitor 18.

In a case where an ON signal Son that is periodically generated by the first system control portion 14A is supplied to the radiation detecting device 30 between the (N−1)th radiographic image capturing event and the Nth radiographic image capturing event, then the light resetting process is carried out based on the ON signal Son.

In a case where the forced resetting switch 158 is operated to supply a forced resetting command signal Sr to the first system control portion 14A between an (N+k)th (k=1, 2, 3, . . . ) radiographic image capturing event and an (N+k+1)th radiographic image capturing event, an ON signal Son is forcibly supplied from the first system control portion 14A to the radiation detecting device 30. Now, the light resetting process is forcibly carried out based on the ON signal Son.

Figure 11:
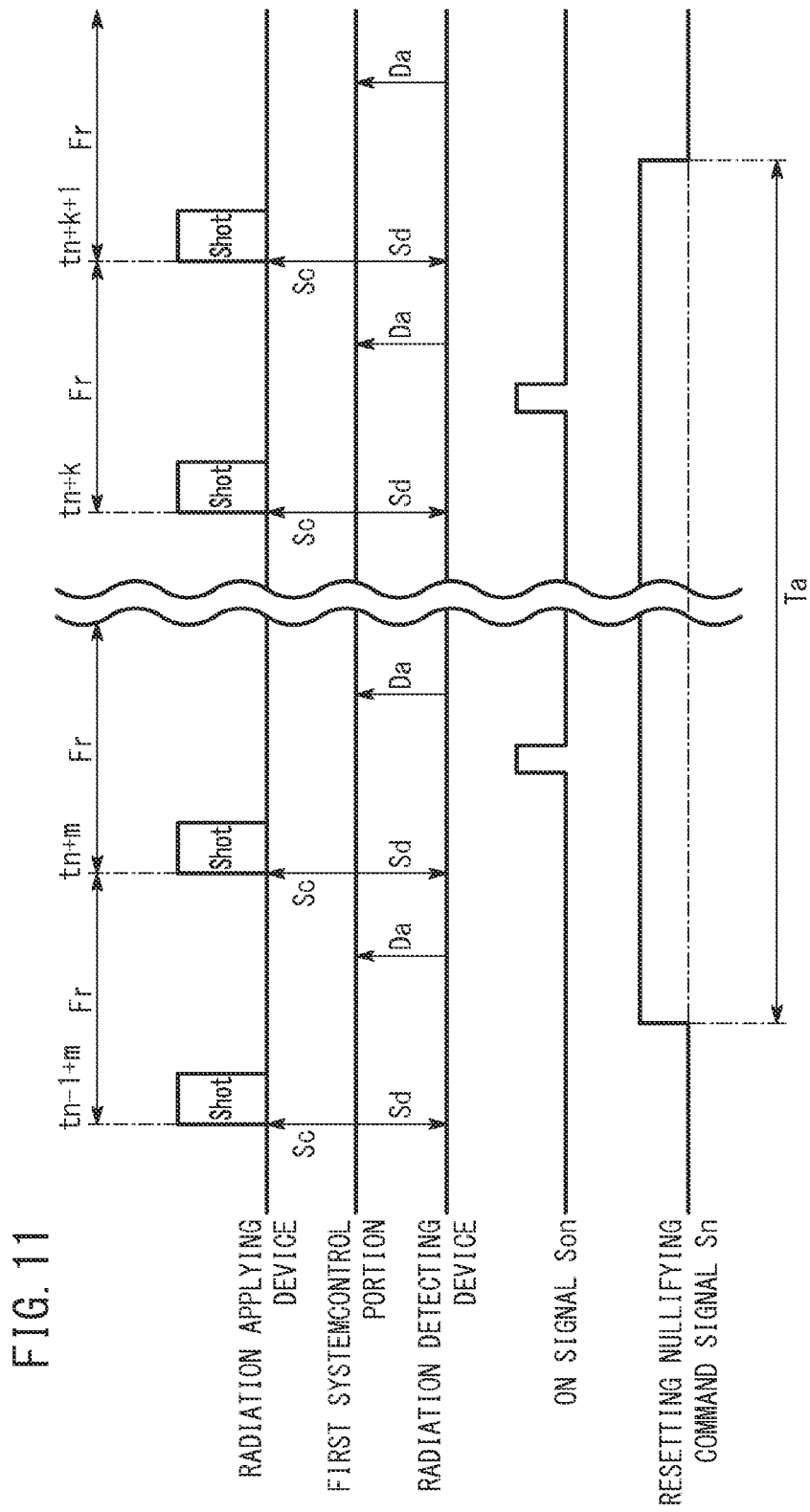
FIG. 11 is a timing chart of a processing sequence of the first system control portion, particularly including operation of a light resetting nullifying portion.

As shown in FIG. 11, in a case where the resetting nullifying switch 156 is operated to supply a resetting nullifying command signal Sn to the first system control portion 14A prior to the start time of an mth (m=50, for example) radiographic image capturing event after the preceding light resetting process, e.g., prior to start time tn+m of an (N+m)th radiographic image capturing event, then the light resetting nullifying portion 162 stops supplying an ON signal Son from the first system control portion 14A, which is otherwise supplied periodically. Therefore, the light resetting process is not performed. The light resetting process is nullified during a period Ta in which it is supplied with the resetting nullifying command signal Sn.

A mode of use of the radiographic image capturing system 10 will be described below with reference to FIGS. 12A and 12B.

Figure 12A:
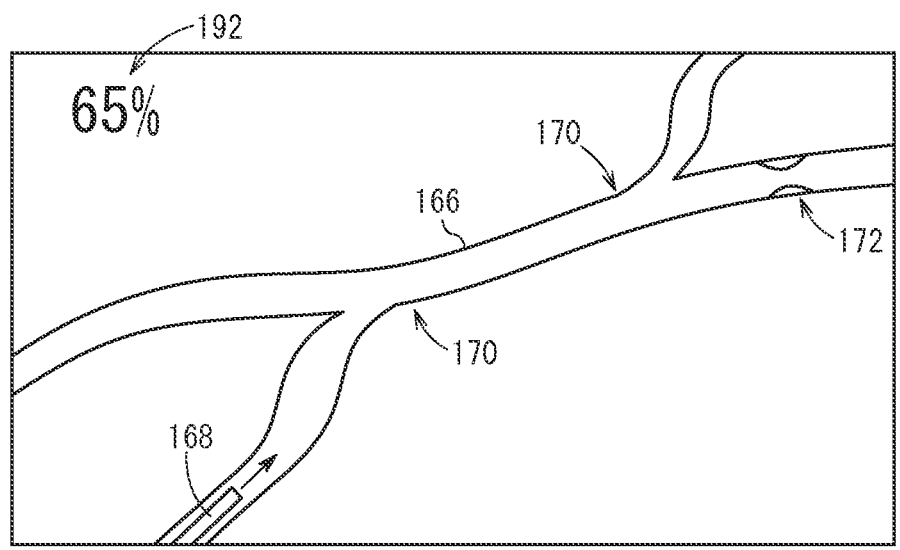
FIGS. 12A and 12B are views showing the manner in which a catheter is inserted into a blood vessel.
Figure 12B:
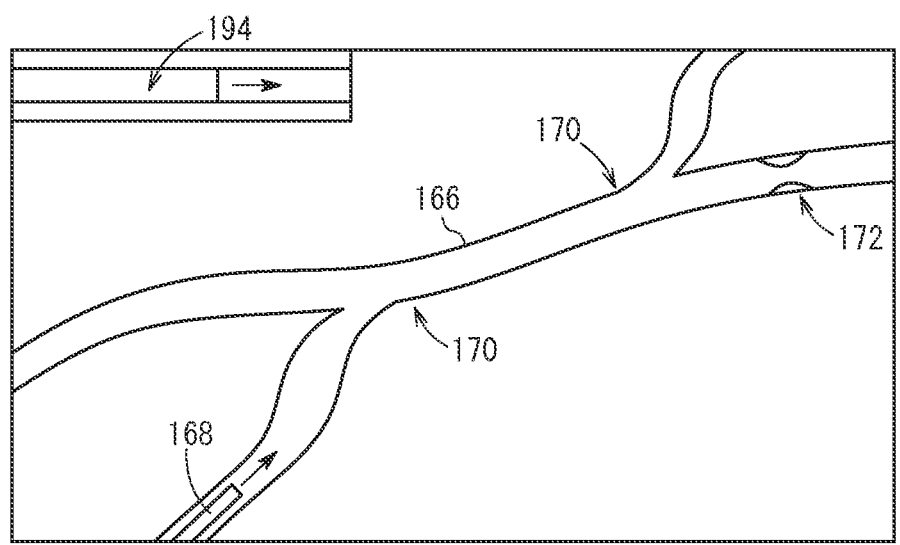

According to one mode of use of the radiographic image capturing system 10, as shown in FIGS. 12A and 12B, a doctor inserts a catheter 168 into a blood vessel 166 in the subject 24, and the doctor visually recognizes the way in which the catheter 168 moves in the blood vessel 166 in real time by observing a radiographic moving image that is being captured by the radiographic image capturing system 10 and displayed on the monitor 18. In a case where the catheter 168 reaches a branch 170 where the blood vessel 166 is bifurcated, the doctor who is handling the catheter 168 carefully controls the catheter 168 to guide it into one of the blood vessels leading from the branch 170 while observing the radiographic moving image displayed on the monitor 18. In a case where the doctor is going to position a stent and a balloon in a constricted region 172 of the blood vessel 166 using the catheter 168, the doctor carefully controls the catheter 168 to guide it into the constricted region 172 while observing the radiographic moving image displayed on the monitor 18.

On the condition that the light resetting process is carried out in the situation described above, then the radiographic image capturing system 10 is unable to capture radiographic images for use as a moving image (fluorography) for a certain period of time that is equal to at least the sum of a period of time in which to apply the resetting light and a period of time in which to remove the effect of the applied resetting light, or even on the condition that the radiographic image capturing system 10 is able to capture radiographic images, the captured radiographic images tend to be disrupted. As a result, the doctor may find it difficult to properly insert the catheter 168 into the blood vessel 166.

In a case where the doctor encounters such a situation in which the light resetting process should not be performed, the doctor turns on the resetting nullifying switch 156 to prevent the light resetting process from being performed. Consequently, the above problems upon light resetting, i.e., the failure to capture radiographic images and the disruption of captured radiographic images, can be avoided in advance in the situation where the doctor needs to move the catheter 168 carefully in the blood vessel 166.

Before the doctor has to move the catheter 168 carefully in the blood vessel 166, the doctor can turn on the forced resetting switch 158 to forcibly perform the light resetting process on the radiation detecting device 30. Therefore, in a case where the doctor needs to observe radiographic images carefully, the radiographic images are prevented from being disrupted by afterimages in advance, so that the doctor can insert the catheter 168 while observing a radiographic moving image of good quality.

Since the ON signal Son from the forced light resetting portion 164 is supplied to the light resetting nullifying portion 162, even on the condition that the doctor turns on the forced resetting switch 158 in error in a situation in which the light resetting process should not be performed, the light resetting process will not forcibly be performed. Consequently, the medical practice will not be obstructed by the light resetting process which would otherwise forcibly be carried out. On the condition that the radiographic moving image cannot clearly be seen by afterimages while the tip end of the catheter 168 is about to enter the branch 170 of the blood vessel 166 in the above mode of use, the doctor can turn off the resetting nullifying switch 156 and turn on the forced resetting switch 158 to perform the light resetting process. Thereafter, it is possible for the doctor to control the catheter 168 while seeing a radiographic moving image that is essentially free of afterimages.

Some system control portions 14 with better operability, i.e., second through fourth system control portions 14B through 14D, according to second through fourth specific examples will be described below with reference to FIGS. 13 through 17.

As shown in FIG. 13, the second system control portion 14B according to the second specific example is of substantially the same configuration as the first system control portion 14A described above, but is different therefrom in that it additionally has a guidance output portion 174 for providing guidance or an indication for turning on the forced resetting switch 158.

The guidance output portion 174 displays an objective numerical value, graph, or the like representing the afterimage phenomenon in radiographic images, so that the doctor can confirm the afterimage phenomenon in radiographic images at a glance.

The guidance output portion 174 may be configured on two principles, i.e., a first principle and a second principle. As shown in FIG. 14A, the guidance output portion 174 that is configured on the first principle has an accumulated dose calculating portion 176 for calculating an accumulated dose that is stored in the radiation detecting device 30 after it has been irradiated with the last resetting light.

According to the present embodiment, the accumulated dose (accumulated exposure dose) refers to an accumulation of doses in successive radiographic image capturing events, i.e., a radiographic moving image capturing event, under a single image capturing technique. The accumulated dose may be, for example, of a value produced in a case where the maximum values of radiation doses detected by the respective pixels 76 of the photoelectric transducing portion 72, i.e., maximum pixel values, are accumulated in radiographic moving image capturing events, or of a value produced in a case where the radiation doses detected by a certain one of the pixels 76 of the photoelectric transducing portion 72 are accumulated in radiographic moving image capturing events.

The accumulated dose calculating portion 176 includes an integrating register 178, a pixel value integrating portion 180, an integrated value resetting portion 182, and a numerical value converting portion 184.

The pixel value integrating portion 180 reads a maximum pixel value or a particular pixel value from among the pixel values of radiographic images Da successively sent from the radiation detecting device 30, adds the read pixel value to an integrated value in the integrating register 178, and stores the sum in the integrating register 178 again.

The integrated value resetting portion 182 resets the integrated value in the integrating register 178 to "0" in response to the ON signal Son supplied from the light resetting nullifying portion 162. Before the moving image capturing process starts, the light resetting nullifying portion 162 is initialized with "0" stored therein.

The numerical value converting portion 184 converts the integrated value in the integrating register 178 into a ratio, e.g., a percentage, to a preset maximum value, and supplies the ratio as information representing an accumulated dose to the console 16. The preset maximum value may be represented by a numerical value that is produced in a case where an upper limit value for pixel values is multiplied by the number of radiographic image capturing events that are carried out in one period of the ON signal Son which is periodically supplied from the ON signal output portion 160.

As shown in FIG. 14B, the guidance output portion 174 that is configured on the second principle has an elapsed time measuring portion 186 for measuring an elapsed time from the last application of the resetting light, a timing register 188, a timing resetting portion 190, and a numerical value converting portion 184.

The elapsed time measuring portion 186 counts reference clock pulses clk and stores the count in the timing register 188. The timing resetting portion 190 resets the count in the timing register 188 to "0" in response to the ON signal Son supplied from the light resetting nullifying portion 162.

The numerical value converting portion 184 converts the count in the timing register 188 into a ratio, e.g., a percentage, to a preset maximum value, and supplies the ratio as information representing an elapsed time to the console 16. The preset maximum value may be represented by the time of one period of the ON signal Son which is periodically supplied from the ON signal output portion 160.

The console 16 displays information of the accumulated dose or information of the elapsed time from the guidance output portion 174 on the monitor 18. Specifically, as shown in FIG. 12A, the console 16 displays the information of the accumulated dose or the information of the elapsed time as a numerical value 192 on an upper left corner, or an upper right corner, of the screen of the monitor 18. Alternatively, as shown in FIG. 12B, the console 16 displays the information of the accumulated dose or the information of the elapsed time as a bar 194 on the upper left corner, or the upper right corner, of the screen of the monitor 18.

In a case where the numerical value 192 shown in FIG. 12A or the bar 194 shown in FIG. 12B is smaller than 70%, for example, the numerical value 192 or the bar 194 is displayed in green. In a case where the numerical value 192 or the bar 194 exceeds 70%, it is displayed in red. In a case where the numerical value 192 or the bar 194 exceeds 90%, it may be blinked.

In the above mode of use of the radiographic image capturing system 10, the doctor carefully inserts the catheter 168 into the blood vessel 166 while observing a radiographic moving image displayed on the monitor 18 in order to guide the catheter 168 accurately into a route to be followed. In a case where the radiographic moving image is adversely affected by afterimages, then the radiographic moving image tends to defocus, making the doctor suffer eye strain. In a case where the doctor turns on the forced resetting switch 158, the light resetting process is performed on the radiation detecting device 30 in advance, and the doctor will not be troubled by afterimages. On the other hand, on the condition that afterimages that are occurring are not strong and do not concern the doctor, then the doctor may not need to turn on the forced resetting switch 158. However, depending on the doctor, or the imaged region, or the level of eye strain, the doctor has to make a subjective judgment as to whether afterimages that are occurring are weak or strong. As a result, the doctor may turn on the forced resetting switch 158 so often that the doctor may possibly find it troublesome to turn on the forced resetting switch 158.

To cope with the above shortcoming, the second system control portion 14B has the guidance output portion 174 which displays the afterimage phenomenon in radiographic images, i.e., the degree of afterimages, as a numerical value or a bar. The doctor can then confirm at a glance the degree of afterimages by seeing the displayed numerical value or bar, and can use the displayed numerical value or bar as a guidance for turning on the forced resetting switch 158. In addition, as the degree of afterimages goes higher, the numerical value or bar is displayed in red or blinked. The doctor can then turn on the forced resetting switch 158 depending on the numerical value or bar that is displayed in red or blinked. Accordingly, the doctor does not feel troublesome about turning on the forced resetting switch 158.

Figure 16:
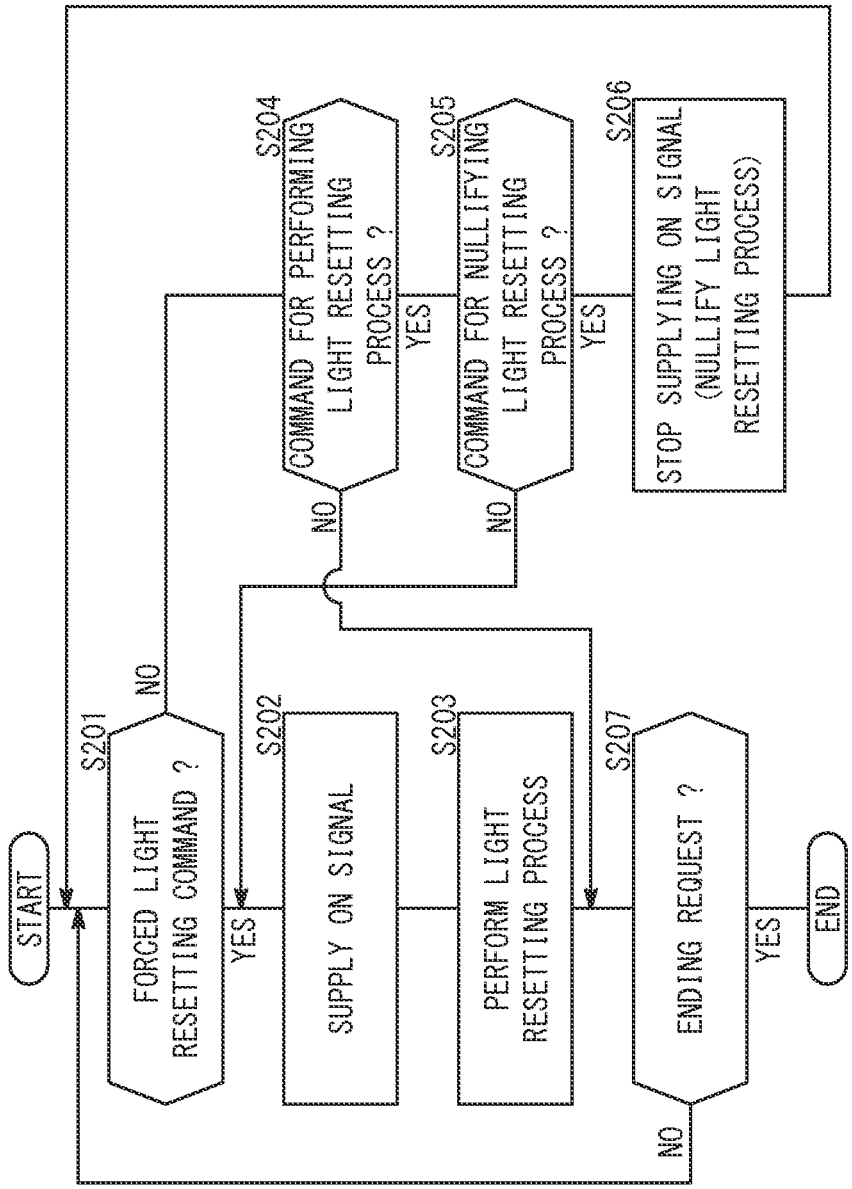
FIG. 16 is a flowchart of a processing sequence of a light resetting processing portion of the third system control portion.

The system control portion according to the third specific example, i.e., the third system control portion 14C, will be described below with reference to FIGS. 15 and 16.

As shown in FIG. 15, the third system control portion 14C is of substantially the same configuration as the second system control portion 14B described above, but is different therefrom in that it additionally has a resetting nullification commanding portion 196 for supplying a resetting nullifying command signal Sn based on the result of an analysis of a radiographic image Da from the radiation detecting device 30, instead of the resetting nullifying switch 156.

The resetting nullification commanding portion 196 supplies a resetting nullifying command signal Sn based on the positional relationship between a designated particular image of the subject 24 and an image of an instrument, e.g., the catheter 168, inserted in the subject 24, in the radiographic image Da from the radiation detecting device 30.

Specifically, the resetting nullification commanding portion 196 includes a range command request portion 198, a particular image setting portion 200, an instrument image setting portion 202, and a resetting nullification determining portion 204.

The range command request portion 198 supplies the console 16 with a request signal Se and a message Dm for requesting the doctor to designate the range of a particular image to the console 16. The console 16 displays the message Dm on the monitor 18. Based on the message Dm displayed on the monitor 18, the doctor designates a range, i.e., a particular image, where the light resetting process is not to be carried out, in the radiographic moving image displayed on the monitor 18. The doctor may designate the range with a displayed surrounding quadrilateral or circular frame that is controlled by drag and drop using the mouse, for example. On the condition that the monitor 18 comprises a touchscreen, then the doctor may designate the range with a displayed circle using a finger or a stylus.

Based on the supplied request signal Se, the console 16 returns address information Dad, which represents a first relative address range of the display area of the monitor 18 with respect to the frame memory and a second relative address range of the particular image with respect to the display area of the monitor 18, to the third system control portion 14C. The address information Dad is supplied to the particular image setting portion 200.

The particular image setting portion 200 specifies an address range of the image displayed on the monitor 18 in the radiographic image Da from the first relative address range in the address information Dad, and sets an address range of the particular image designated by the doctor in the radiographic image Da from the specified address range and the second relative address range.

The instrument image setting portion 202 extracts an image which moves the greatest distance from radiographic images Da in a plurality of frames that are successively supplied, determines an address of a leading tip end of the extracted image, i.e., an address on the latest radiographic image, and uses the determined address as the address of the image of the instrument, i.e., the catheter 168. The image which moves the greatest distance should preferably be extracted according to a motion vector search which is used in a known interframe prediction process.

In a case where the address of the image of the instrument is not included in the address range of the particular image designated by the doctor, then the resetting nullification determining portion 204 does not supply the resetting nullifying command signal Sn. On the condition that the address of the image of the instrument is included in the address range of the particular image designated by the doctor, then the resetting nullification determining portion 204 supplies the resetting nullifying command signal Sn. In particular, the resetting nullification determining portion 204 continues to supply the resetting nullifying command signal Sn during a period Ta in which the address of the image of the instrument is included in the address range of the particular image.

In the above mode of use of the radiographic image capturing system 10, simply in a case where the doctor designates a range, i.e., a particular image, in which the light resetting process is not to be carried out, in the radiographic moving image displayed on the monitor 18 using a mouse or touch panel, the third system control portion 14C automatically keeps supplying the resetting nullifying command signal Sn during the period Ta after the tip end of the catheter 168 enters the designated range until it leaves the designated range. During the period Ta, therefore, the light resetting process is not carried out. Since the doctor does not need to turn on the resetting nullifying switch 156 during the period Ta, the doctor may give their full attention to controlling the catheter 168.

Since unlike the first system control portion 14A, the third system control portion 14C does not make it necessary for the doctor to turn on the resetting nullifying switch 156, on the condition that the radiographic moving image cannot clearly be seen by afterimages while the tip end of the catheter 168 is about to enter the branch 170 of the blood vessel 166, the doctor cannot turn off the resetting nullifying switch 156 and turn on the forced resetting switch 158. To cope with the above problem, the third system control portion 14C supplies the ON signal Son from the forced light resetting portion 164 directly, not via the light resetting nullifying portion 162, to the radiation detecting device 30, thereby forcibly carrying out the light resetting process. Consequently, even though the resetting nullifying command signal Sn is supplied to the light resetting nullifying portion 162, the light resetting process is forcibly carried out in a case where the doctor turns on the forced resetting switch 158, and hence the doctor will not be troubled by afterimages.

A processing sequence of the light resetting processing portion 148 of the third system control portion 14C will be described below with reference to FIG. 16. In step S201 shown in FIG. 16, the forced light resetting portion 164 judges whether there is a forced light resetting command or not by judging whether there is supplied a forced resetting command signal Sr or not.

In a case where the forced light resetting portion 164 judges that there is supplied a forced resetting command signal Sr, then control goes to step S202 in which the forced light resetting portion 164 supplies an ON signal Son for performing the light resetting process to the radiation detecting device 30. In step S203, the photoelectric transducing portion 72 is reset by being irradiated with resetting light.

In a case where the forced light resetting portion 164 judges that there is not a forced light resetting command in step S201, then control goes to step S204 in which the light resetting nullifying portion 162 judges whether there is a command for performing the light resetting process or not. Specifically, the light resetting nullifying portion 162 judges whether it is supplied with an ON signal Son from the ON signal output portion 160 or not. On the condition that the light resetting nullifying portion 162 is supplied with an ON signal Son, i.e., a command for performing the light resetting process, then control goes to step S205 in which the light resetting nullifying portion 162 judges whether there is a command for nullifying the light resetting process or not. Specifically, the light resetting nullifying portion 162 judges whether it is being supplied with a resetting nullifying command signal Sn or not. On the condition that the light resetting nullifying portion 162 is supplied with a resetting nullifying command signal Sn, i.e., a command for nullifying the light resetting process, then control goes to step S206 in which the supply of the ON signal Son is stopped, nullifying the command for performing the light resetting process. Thereafter, control goes back to step S201 to repeat the processing from step S201.

On the condition that the light resetting nullifying portion 162 judges that it is not supplied with a command for nullifying the light resetting process in step S205, then control goes to steps S202, S203 to reset the photoelectric transducing portion 72 by irradiating it with resetting light.

On the condition that the light resetting nullifying portion 162 judges that it is not supplied with a command for performing the light resetting process in step S204 or on the condition that where the photoelectric transducing portion 72 has been reset by being irradiated with resetting light in step S203, control goes to step S207. In step S207, the third system control portion 14C judges whether there is a request for ending the moving image capturing process or not. On the condition that there is not a request for ending the moving image capturing process, then control goes back to step S201 to repeat the light resetting process from step S201. On the condition that there is a request for ending the moving image capturing process in step S207, then the light resetting process is ended.

The system control portion according to the fourth specific example, i.e., the fourth system control portion 14D, will be described below with reference to FIG. 17.

Figure 17:
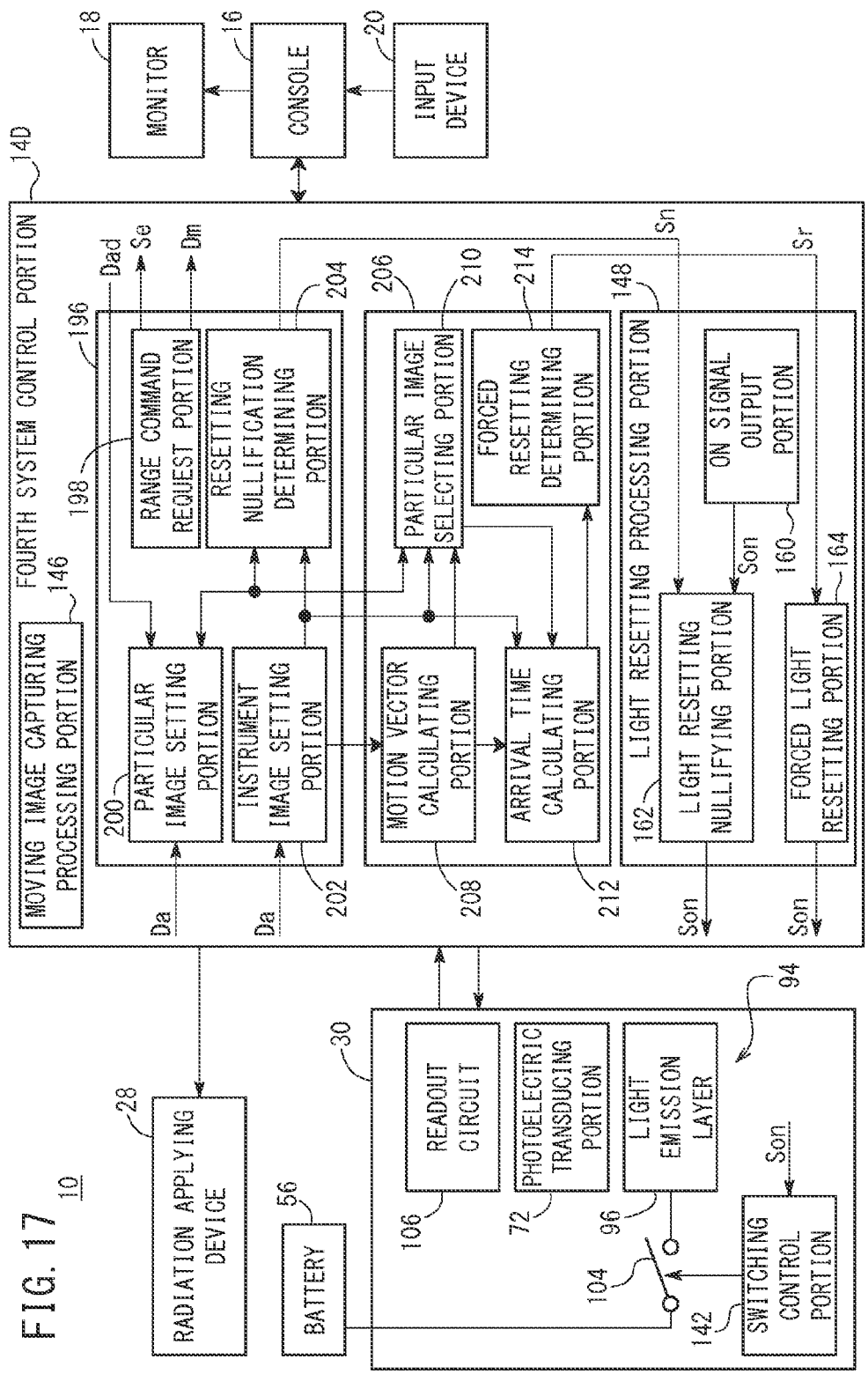
FIG. 17 is a block diagram showing mainly the configuration of a fourth system control portion.

As shown in FIG. 17, the fourth system control portion 14D is of substantially the same configuration as the third system control portion 14C described above, but is different therefrom in that it has a forced resetting commanding portion 206 for supplying a forced resetting command signal Sr based on the result of an analysis of a radiographic image Da, instead of the forced resetting switch 158 shown in FIG. 15. In FIG. 17, the details of the moving image capturing processing portion 146 are omitted from illustration.

The forced resetting commanding portion 206 supplies a forced resetting command signal Sr based on the positional relationship between a designated particular image of the subject 24 and an image of an instrument, e.g., the catheter 168, inserted in the subject 24, in the radiographic image Da from the radiation detecting device 30.

Specifically, the forced resetting commanding portion 206 includes a motion vector calculating portion 208, a particular image selecting portion 210, an arrival time calculating portion 212, and a forced resetting determining portion 214.

The motion vector calculating portion 208 determines a moving direction and a moving speed of the instrument image based on an address of the instrument image determined by the instrument image setting portion 202 of the resetting nullification commanding portion 196. The address of the instrument image that is supplied from the instrument image setting portion 202 changes from time to time, frame by frame. Therefore, the motion vector calculating portion 208 determines a moving direction and a moved distance of the instrument image based on the address that changes from time to time, and determines a moving speed of the instrument image based on the moved distance and the latest frame rate.

The particular image selecting portion 210 selects an address range of a closest particular image that is present in the moving direction of the instrument image, based on an address range of one or more particular images set by the particular image setting portion 200 of the resetting nullification commanding portion 196, the address of the instrument image determined by the instrument image setting portion 202, and the moving direction of the instrument image from the motion vector calculating portion 208.

The arrival time calculating portion 212 calculates a distance up to the particular image selected from the instrument image based on the address of the instrument image and the address range of the selected particular image, and also calculates an arrival time based on the calculated distance and the moving speed of the instrument image from the motion vector calculating portion 208.

The forced resetting determining portion 214 supplies a forced resetting command signal Sr in a case where the arrival time calculated by the arrival time calculating portion 212 reaches a preset time, thereby forcibly performing the light resetting process. The preset time should preferably be at least the sum of a period of time (the pulse duration of a pulse signal) in which the resetting light is applied and a period of time in which the effect of the applied resetting light is removed.

In the mode of use of the radiographic image capturing system 10, before the doctor has to move the catheter 168 carefully in the blood vessel 166, the fourth system control portion 14D automatically and forcibly performs the light resetting process simply in a case where the doctor designates a range, i.e., a particular image, in which the light resetting process is not to be carried out, in the radiographic moving image displayed on the monitor 18 using a mouse or touch panel. Therefore, in a case where the doctor needs to observe radiographic images carefully, the radiographic images are prevented from being disrupted by afterimages in advance, so that the doctor can insert the catheter 168 while observing a radiographic moving image of good quality. Since the doctor does not need to turn on the forced resetting switch 158 as well as the resetting nullifying switch 156, the doctor may give their full attention to controlling the catheter 168.

In the above embodiment, the fight resetting processing portion 148 and the guidance output portion 174 are incorporated in the system control portion 14. However, as shown in FIG. 18, the light resetting processing portion 148 and the guidance output portion 174 may be incorporated in the cassette control portion 68 of the radiation detecting device 30.

Figure 18:
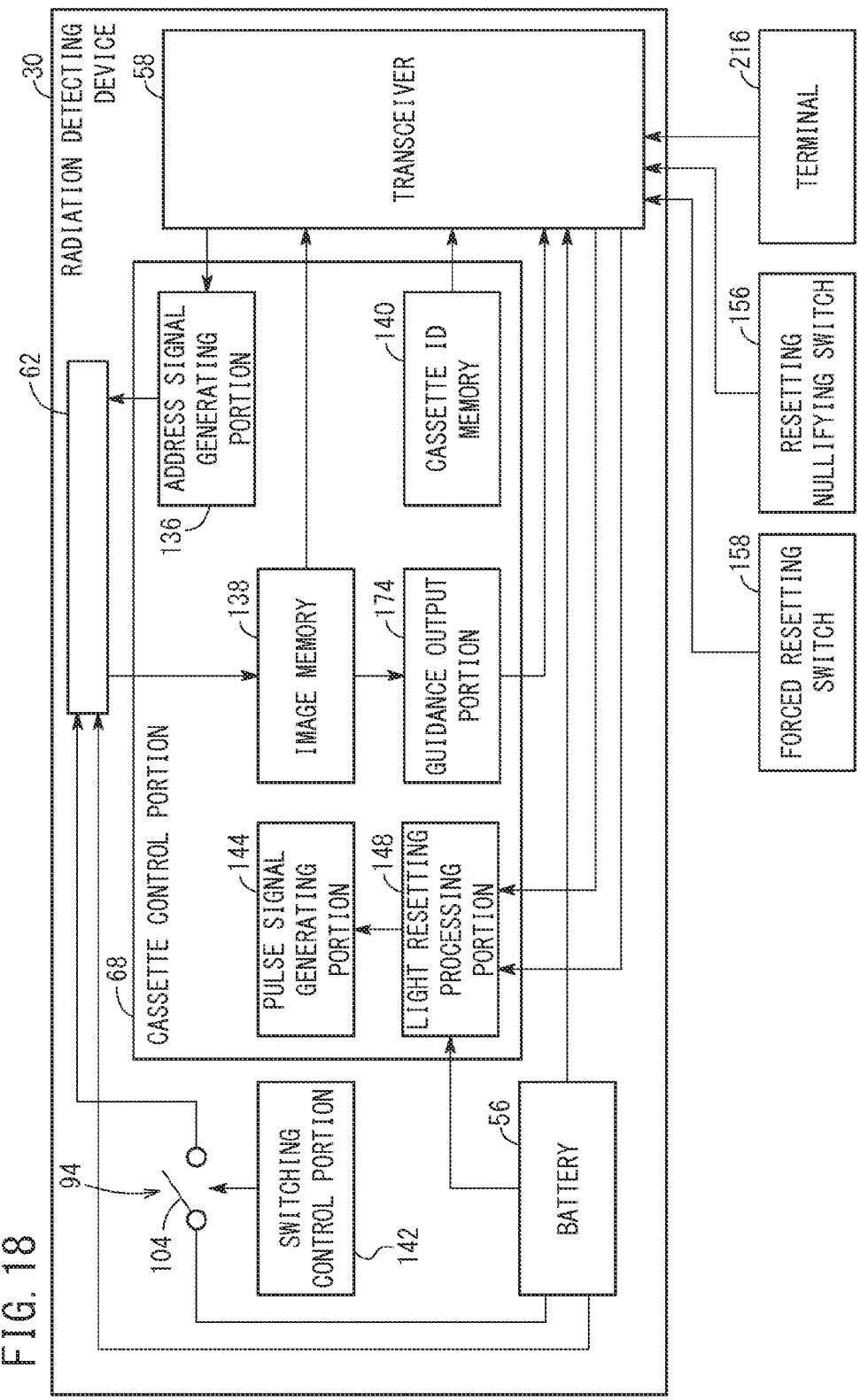
FIG. 18 is a block diagram showing the configuration of a radiation applying device according to another embodiment of the present invention.

Specifically, as shown in FIG. 18, the cassette control portion 68 includes the light resetting processing portion 148 and the guidance output portion 174 in addition to the address signal generating portion 136, the image memory 138, the cassette ID memory 140, and the pulse signal generating portion 144. The radiation detecting device 30 has the resetting nullifying switch 156 and the forced resetting switch 158 that are disposed in the casing 40 or outside the casing 40. On the condition that the resetting nullifying switch 156 and the forced resetting switch 158 are disposed outside the casing 40, they are electrically connected to the radiation detecting device 30 via a wired communication link or a wireless communication link. A mobile terminal 216 having a display portion is also electrically connected to the radiation detecting device 30 via a wired communication link or a wireless communication link.

The mobile terminal 216 may display radiographic images sent through the console for displaying a radiographic moving image, and may display radiographic images sent directly from the radiation detecting device for displaying a radiographic moving image. The mobile terminal 216 may also display guidance as shown in FIGS. 12A and 12B.

The resetting nullification commanding portion 196 of the third system control portion 14C or the forced resetting commanding portion 206 of the fourth system control portion 14D may also be incorporated in the cassette control portion 68.

The radiographic image capturing systems and the radiation detecting devices according to the present invention are not limited to the above embodiments, but may employ various arrangements without departing from the scope of the invention.

The invention claimed is:

1. A radiographic image capturing system comprising:
a radiographic image capturing apparatus including a radiation applying device having a radiation source and a radiation detecting device for converting radiation emitted from the radiation source and transmitted through a subject into a radiographic image and supplying the radiographic image; and
a system control portion for controlling the radiographic image capturing apparatus to perform a radiographic image capturing process at a preset frame rate;
wherein the radiation detecting device has a scintillator for converting the radiation into fluorescence, a photoelectric transducing portion for converting the fluorescence into an electric signal, and a resetting light source for irradiating the photoelectric transducing portion with resetting light; and
the system control portion has a light resetting nullifying portion for nullifying application of the resetting light from the resetting light source in response to a resetting nullifying command,
wherein the system control portion further includes:
a resetting nullification commanding portion for supplying the resetting nullifying command based on a result of an analysis of the radiographic image from the radiation detecting device,
wherein the light resetting nullifying portion nullifies the application of the resetting light from the resetting light source in response to the resetting nullifying command,
wherein the resetting nullification commanding portion supplies the resetting nullifying command based on a positional relationship between a designated particular image of the subject in the radiographic image from the radiation detecting device and an image of an instrument inserted in the subject.

2. The radiographic image capturing system according to claim 1, wherein the resetting nullification commanding portion supplies the resetting nullifying command during a period in which the designated particular image of the subject and the image of the instrument inserted in the subject are in a preset positional relationship; and
wherein the light resetting nullifying portion nullifies the application of the resetting light from the resetting light source only during a period in which the resetting nullifying command is supplied.

3. The radiographic image capturing system according to claim 2, wherein the preset positional relationship is a relationship in which the image of the instrument has a portion placed in the particular image.

4. The radiographic image capturing system according to claim 1, further comprising:
a forced light resetting portion for forcibly applying the resetting light from the resetting light source in response to a forced resetting command.

5. The radiographic image capturing system according to claim 4, further comprising:
a forced resetting switch for supplying the forced resetting command in response to an operator's input;
wherein the forced light resetting portion forcibly applies the resetting light from the resetting light source in response to the forced resetting command from the forced resetting switch.

6. The radiographic image capturing system according to claim 5, wherein the system control portion further includes:
a guidance output portion for providing guidance for turning on the forced resetting switch.

7. The radiographic image capturing system according to claim 6, wherein the guidance comprises an afterimage phenomenon in the radiographic image.

8. The radiographic image capturing system according to claim 7, wherein the guidance output portion includes:
an accumulated dose calculating portion for calculating an accumulated dose that is stored in the radiation detecting device after the radiation detecting device has been irradiated with last resetting light; and
wherein the guidance output portion supplies the accumulated dose as representing the afterimage phenomenon in the radiographic image.

9. The radiographic image capturing system according to claim 6, wherein the guidance comprises an elapsed time from the application of last resetting light.

10. The radiographic image capturing system according to claim 4, wherein the system control portion further includes:
a forced resetting commanding portion for supplying the forced resetting command based on the result of an analysis of the radiographic image from the radiation detecting device.

11. The radiographic image capturing system according to claim 10, wherein the forced resetting commanding portion supplies the forced resetting command based on a positional relationship between a designated particular image of the subject in the radiographic image from the radiation detecting device and an image of an instrument inserted in the subject.

12. The radiographic image capturing system according to claim 11, wherein the forced resetting commanding portion includes:
a motion vector calculating portion for determining a moving direction and a moving speed of the image of the instrument based on a plurality of radiographic images; and
wherein the forced resetting commanding portion supplies the forced resetting command in a case where the moving direction of the image of the instrument is oriented toward the particular image and before the image of the instrument reaches the particular image.

13. The radiographic image capturing system according to claim 12, wherein the forced resetting commanding portion supplies the forced resetting command in a case where the moving direction of the image of the instrument is oriented toward the particular image and a time required until the image of the instrument reaches the particular image becomes a preset time.

14. A radiation detecting device comprising:
a scintillator for converting radiation into fluorescence;
a photoelectric transducing portion for converting the fluorescence into an electric signal;

a resetting light source for irradiating the photoelectric transducing portion with resetting light;

a light resetting nullifying portion for nullifying application of the resetting light from the resetting light source in response to a resetting nullifying command;

a forced light resetting portion for forcibly applying the resetting light from the resetting light source in response to a forced resetting command;

a forced resetting switch for supplying the forced resetting command in response to operator's input; and a guidance output portion for providing guidance for turning on the forced resetting switch, wherein the forced light resetting portion forcibly applies the resetting light from the resetting light source in response to the forced resetting command from the forced resetting switch.

15. The radiation detecting device according to claim 14, wherein the guidance comprises an afterimage phenomenon in the radiographic image.

16. The radiation detecting device according to claim 15, wherein the guidance output portion includes:

an accumulated dose calculating portion for calculating an accumulated dose that is stored in the radiation detecting device after application of last resetting light; and wherein the guidance output portion supplies the accumulated dose as representing the afterimage phenomenon in the radiographic image.

17. The radiation detecting device according to claim 14, wherein the guidance comprises an elapsed time from the application of last resetting light.

\* \* \* \* \*